(12) United States Patent
Xu et al.

(10) Patent No.: US 7,898,661 B2
(45) Date of Patent: Mar. 1, 2011

(54) SPECTROSCOPIC SCATTEROMETER SYSTEM

(75) Inventors: Yiping Xu, Cupertino, CA (US);
Ibrahim Abdulhalm, Kfar Manda (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/642,670

(22) Filed: Dec. 18, 2009

(65) Prior Publication Data

US 2010/0165340 A1 Jul. 1, 2010

Related U.S. Application Data

(63) Continuation of application No. 11/614,315, filed on Dec. 21, 2006, which is a continuation of application No. 10/251,246, filed on Sep. 20, 2002, now Pat. No. 7,173,699, which is a continuation of application No. 09/036,557, filed on Mar. 6, 1998, now Pat. No. 6,483,580.

(51) Int. Cl.
*G01J 4/00* (2006.01)

(52) U.S. Cl. ...................................................... 356/369

(58) Field of Classification Search .................. 356/300, 356/319, 326, 328, 364–369, 445–448
See application file for complete search history.

(56) References Cited

U.S. PATENT DOCUMENTS

| | | | |
|---|---|---|---|
| 3,426,201 A | 2/1969 | Hilton et al. | |
| 3,547,074 A | 12/1970 | Hirschfeld | |
| 3,667,846 A | 6/1972 | Nater et al. | |
| 3,671,126 A | 6/1972 | Erb | |
| 4,039,370 A | 8/1977 | Kleinknecht | |
| 4,141,780 A | 2/1979 | Kleinknecht et al. | |
| 4,146,327 A | 3/1979 | Harris | |
| 4,149,089 A | 4/1979 | Idelsohn et al. | |
| 4,168,437 A | 9/1979 | Nihonmatsu | |
| 4,171,917 A | 10/1979 | Pirlet | |
| 4,173,788 A | 11/1979 | Laliotis | |
| 4,200,396 A | 4/1980 | Kleinknecht et al. | |
| 4,303,341 A | 12/1981 | Kleinknecht et al. | |
| 4,330,213 A | 5/1982 | Kleinknecht et al. | |
| 4,373,804 A | 2/1983 | Pryor et al. | |

(Continued)

FOREIGN PATENT DOCUMENTS

DE 41 05 192 A1 8/1991

(Continued)

OTHER PUBLICATIONS

European Patent Office, "Communication of the European Search Report" mailed in related European Application No. 04078145.2 on Dec. 28, 2004, 3 pages.

(Continued)

*Primary Examiner* — Tu T Nguyen
(74) *Attorney, Agent, or Firm* — Davis Wright Tremaine LLP

(57) ABSTRACT

Before the diffraction from a diffracting structure on a semiconductor wafer is measured, where necessary, the film thickness and index of refraction of the films underneath the structure are first measured using spectroscopic reflectometry or spectroscopic ellipsometry. A rigorous model is then used to calculate intensity or ellipsometric signatures of the diffracting structure. The diffracting structure is then measured using a spectroscopic scatterometer using polarized and broadband radiation to obtain an intensity or ellipsometric signature of the diffracting structure. Such signature is then matched with the signatures in the database to determine the grating shape parameters of the structure.

28 Claims, 5 Drawing Sheets

U.S. PATENT DOCUMENTS

| | | |
|---|---|---|
| 4,408,884 A | 10/1983 | Kleinknecht et al. |
| 4,516,855 A | 5/1985 | Korth |
| 4,615,620 A | 10/1986 | Noguchi et al. |
| 4,634,232 A | 1/1987 | Tateoka |
| 4,650,335 A | 3/1987 | Ito et al. |
| 4,653,924 A | 3/1987 | Itonaga et al. |
| 4,655,595 A | 4/1987 | Bjork et al. |
| 4,668,860 A | 5/1987 | Anthon |
| 4,672,196 A | 6/1987 | Canino |
| 4,687,325 A | 8/1987 | Corby, Jr. |
| 4,689,491 A | 8/1987 | Lindow et al. |
| 4,695,162 A | 9/1987 | Itonaga et al. |
| 4,710,642 A | 12/1987 | McNeil |
| 4,790,659 A | 12/1988 | Erman et al. |
| 4,905,170 A | 2/1990 | Forouhi et al. |
| 4,964,726 A | 10/1990 | Kleinknecht et al. |
| RE33,424 E | 11/1990 | Noguchi et al. |
| 4,991,971 A | 2/1991 | Geary et al. |
| 4,999,014 A | 3/1991 | Gold et al. |
| 5,007,708 A | 4/1991 | Gaylord |
| 5,018,863 A | 5/1991 | Vareille et al. |
| 5,032,734 A | 7/1991 | Orazio, Jr. et al. |
| 5,042,951 A | 8/1991 | Gold et al. |
| 5,076,696 A | 12/1991 | Cohn et al. |
| 5,087,121 A | 2/1992 | Kakuchi et al. |
| 5,091,320 A | 2/1992 | Aspnes et al. |
| 5,125,040 A | 6/1992 | Matsui et al. |
| 5,164,579 A | 11/1992 | Pryor et al. |
| 5,164,790 A | 11/1992 | McNeil et al. |
| 5,166,199 A | 11/1992 | Kasch et al. |
| 5,166,752 A | 11/1992 | Spanier et al. |
| 5,170,049 A | 12/1992 | De Jonge et al. |
| 5,173,719 A | 12/1992 | Taniguchi et al. |
| 5,241,369 A | 8/1993 | McNeil et al. |
| 5,270,794 A | 12/1993 | Tsuji et al. |
| 5,280,179 A | 1/1994 | Pryor et al. |
| 5,313,044 A | 5/1994 | Massoud et al. |
| 5,329,357 A | 7/1994 | Bernoux et al. |
| 5,333,052 A | 7/1994 | Finarov |
| 5,337,146 A | 8/1994 | Azzam |
| 5,337,150 A | 8/1994 | Mumola |
| 5,355,212 A | 10/1994 | Wells et al. |
| 5,361,137 A | 11/1994 | Aton et al. |
| 5,362,970 A | 11/1994 | Pryor et al. |
| 5,363,171 A | 11/1994 | Mack |
| 5,365,340 A | 11/1994 | Ledger |
| 5,381,233 A | 1/1995 | Chao et al. |
| 5,386,317 A | 1/1995 | Corle et al. |
| 5,393,624 A | 2/1995 | Ushijima |
| 5,399,229 A | 3/1995 | Stefani et al. |
| 5,408,322 A | 4/1995 | Hsu et al. |
| 5,412,473 A | 5/1995 | Rosencwaig et al. |
| 5,416,594 A | 5/1995 | Gross et al. |
| 5,420,680 A | 5/1995 | Isobe et al. |
| 5,432,607 A | 7/1995 | Taubenblatt |
| 5,438,415 A | 8/1995 | Kazama et al. |
| 5,450,201 A | 9/1995 | Katzir et al. |
| 5,486,919 A | 1/1996 | Tsuji et al. |
| 5,494,697 A | 2/1996 | Blayo et al. |
| 5,503,707 A | 4/1996 | Maung et al. |
| 5,504,582 A | 4/1996 | Johs et al. |
| 5,510,625 A | 4/1996 | Pryor et al. |
| 5,517,312 A | 5/1996 | Finarov |
| 5,519,793 A | 5/1996 | Grannes |
| 5,521,706 A | 5/1996 | Green et al. |
| 5,526,117 A | 6/1996 | Wielsch et al. |
| 5,555,472 A | 9/1996 | Clapis |
| 5,596,411 A | 1/1997 | Fanton et al. |
| 5,604,581 A | 2/1997 | Liu et al. |
| 5,607,800 A | 3/1997 | Ziger |
| 5,608,526 A | 3/1997 | Piwonka-Corle et al. |
| 5,610,392 A | 3/1997 | Nagayama et al. |
| 5,625,453 A | 4/1997 | Matsumoto et al. |
| 5,625,455 A | 4/1997 | Nash et al. |
| 5,631,171 A | 5/1997 | Sandstrom et al. |
| 5,638,178 A | 6/1997 | Lacey et al. |
| 5,638,199 A | 6/1997 | Tsubota et al. |
| 5,654,903 A | 8/1997 | Reitman et al. |
| 5,666,199 A | 9/1997 | Hess et al. |
| 5,666,200 A | 9/1997 | Drevillon et al. |
| 5,666,201 A | 9/1997 | Johs et al. |
| 5,670,787 A | 9/1997 | Pryor et al. |
| 5,674,652 A | 10/1997 | Bishop et al. |
| 5,677,541 A | 10/1997 | Pryor et al. |
| 5,691,545 A | 11/1997 | Pryor et al. |
| 5,693,953 A | 12/1997 | Pryor et al. |
| 5,703,692 A | 12/1997 | McNeil et al. |
| 5,734,172 A | 3/1998 | Pryor et al. |
| 5,739,909 A | 4/1998 | Blayo et al. |
| 5,747,813 A | 5/1998 | Norton et al. |
| 5,754,296 A | 5/1998 | Law |
| 5,757,671 A | 5/1998 | Drevillon et al. |
| 5,767,525 A | 6/1998 | Pryor et al. |
| 5,773,840 A | 6/1998 | Pryor et al. |
| 5,777,744 A | 7/1998 | Yoshii et al. |
| 5,786,602 A | 7/1998 | Pryor et al. |
| 5,805,290 A | 9/1998 | Ausschnitt et al. |
| 5,811,825 A | 9/1998 | Pryor et al. |
| 5,811,827 A | 9/1998 | Pryor et al. |
| 5,825,498 A | 10/1998 | Thakur et al. |
| 5,835,220 A | 11/1998 | Kazama et al. |
| 5,835,221 A | 11/1998 | Lee et al. |
| 5,854,491 A | 12/1998 | Pryor et al. |
| 5,866,915 A | 2/1999 | Pryor et al. |
| 5,866,916 A | 2/1999 | Pryor et al. |
| 5,867,276 A | 2/1999 | McNeil et al. |
| 5,877,491 A | 3/1999 | Pryor et al. |
| 5,880,459 A | 3/1999 | Pryor et al. |
| 5,880,838 A | 3/1999 | Marx et al. |
| 5,883,390 A | 3/1999 | Pryor et al. |
| 5,923,423 A | 7/1999 | Sawatari et al. |
| 5,956,148 A | 9/1999 | Celii |
| 5,963,329 A | 10/1999 | Conrad et al. |
| 5,981,965 A | 11/1999 | Pryor et al. |
| 5,982,496 A | 11/1999 | Ziger |
| 6,031,615 A | 2/2000 | Meeks et al. |
| 6,100,985 A | 8/2000 | Scheiner et al. |
| 6,104,486 A | 8/2000 | Arimoto |
| 6,118,525 A | 9/2000 | Fossey et al. |
| 6,127,689 A | 10/2000 | Pryor et al. |
| 6,138,055 A | 10/2000 | Pryor |
| 6,157,451 A | 12/2000 | Mizuno |
| 6,211,506 B1 | 4/2001 | Pryor et al. |
| 6,263,099 B1 | 7/2001 | Maeda et al. |
| 6,271,047 B1 | 8/2001 | Ushio et al. |
| 6,278,519 B1 | 8/2001 | Rosencwaig et al. |
| 6,323,946 B1 | 11/2001 | Norton |
| 6,476,920 B1 | 11/2002 | Scheiner et al. |
| 6,483,580 B1 | 11/2002 | Xu et al. |
| 6,590,656 B2 * | 7/2003 | Xu et al. ............ 356/369 |
| 6,594,012 B2 | 7/2003 | Takeuchi et al. |
| 6,603,542 B1 | 8/2003 | Chase et al. |
| 6,614,540 B1 | 9/2003 | Stirton |
| 6,657,736 B1 | 12/2003 | Finarov et al. |
| 6,678,043 B1 | 1/2004 | Vurens et al. |
| 6,728,663 B2 | 4/2004 | Krukar et al. |
| 6,819,426 B2 | 11/2004 | Sezginer et al. |
| 6,829,057 B2 | 12/2004 | Opsal et al. |
| 6,836,324 B2 | 12/2004 | Scheiner et al. |
| 6,900,892 B2 | 5/2005 | Shchegrov et al. |
| 6,982,792 B1 | 1/2006 | Woollam et al. |
| 7,003,149 B2 | 2/2006 | Benesch et al. |
| 7,099,005 B1 | 8/2006 | Fabrikant et al. |
| 7,123,366 B2 | 10/2006 | Scheiner et al. |
| 7,173,699 B2 | 2/2007 | Xu et al. |
| 7,187,456 B2 | 3/2007 | Scheiner et al. |
| 7,242,477 B2 | 7/2007 | Mieher et al. |
| 7,280,212 B2 | 10/2007 | Mieher et al. |
| 7,280,230 B2 | 10/2007 | Shchegrov et al. |
| 7,298,213 B2 | 11/2007 | Kang |
| 7,298,481 B2 | 11/2007 | Mieher et al. |
| 7,301,634 B2 | 11/2007 | Mieher et al. |
| 7,372,579 B2 | 5/2008 | Chen et al. |
| 7,515,253 B2 | 4/2009 | Bareket et al. |
| 2002/0113966 A1 | 8/2002 | Shchegrov et al. |
| 2009/0135416 A1 | 5/2009 | Shchegrov et al. |

FOREIGN PATENT DOCUMENTS

| | | |
|---|---|---|
| DE | 41 08 329 A1 | 9/1992 |
| EP | 0061237 B1 | 4/1986 |
| EP | 0021205 A1 | 12/1986 |
| EP | 0300508 A2 | 1/1989 |
| EP | 0403769 A2 | 12/1990 |
| EP | 0458418 A2 | 11/1991 |
| EP | 0480620 A2 | 4/1992 |
| EP | 0480620 A3 | 9/1992 |
| EP | 0660077 A2 | 6/1995 |
| EP | 1124163 A2 | 8/2001 |
| EP | 1073876 B1 | 12/2004 |
| EP | 1508772 A1 | 2/2005 |
| EP | 1124163 A3 | 7/2005 |
| FR | 2 597 976 A1 | 10/1987 |
| FR | 2 731 074 A1 | 8/1996 |
| JP | 54092286 A | 7/1979 |
| JP | 57187604 A | 11/1982 |
| JP | 58206120 A | 12/1983 |
| JP | 59140420 | 8/1984 |
| JP | 60033003 A | 2/1985 |
| JP | 60074528 A | 4/1985 |
| JP | 60086843 A | 5/1985 |
| JP | 60128602 A | 7/1985 |
| JP | 60166808 A | 8/1985 |
| JP | 60236005 A | 11/1985 |
| JP | 61004905 A | 1/1986 |
| JP | 61004906 A | 1/1986 |
| JP | 61039852 A | 2/1986 |
| JP | 62150251 A | 7/1987 |
| JP | 63308507 A | 12/1988 |
| JP | 1026102 A | 1/1989 |
| JP | 1182707 A | 7/1989 |
| JP | 01211937 | 8/1989 |
| JP | 01285806 | 11/1989 |
| JP | 02012002 | 1/1990 |
| JP | 03075504 A | 3/1991 |
| JP | 04042945 A | 2/1992 |
| JP | 04176143 | 6/1992 |
| JP | 05023620 | 4/1993 |
| JP | 06147987 | 5/1994 |
| JP | 07022483 | 1/1995 |
| JP | 07074088 | 3/1995 |
| JP | 07231023 | 8/1995 |
| JP | 07270144 | 10/1995 |
| JP | H08-255751 A | 10/1996 |
| JP | H08-261727 A | 10/1996 |
| JP | H09-237812 A | 9/1997 |
| JP | 11119213 | 4/1999 |
| SU | 1146549 A | 3/1985 |
| SU | 1226042 A | 4/1986 |
| SU | 1695145 A1 | 11/1991 |
| WO | WO 99/45340 | 9/1999 |
| WO | WO 00/35002 | 6/2000 |

OTHER PUBLICATIONS

European Patent Office, "Office Action" mailed in related European Patent Application No. 04078145.2 on Jun. 26, 2007, 18 pages (including pending claims).
Japan Patent Office, "Decision of Refusal" mailed in related Japanese Patent Application No. 2000-534831 on Jun. 23, 2009, 20 pages (including pending claims).
Japan Patent Office, "Final Notification of Reasons for Refusal" mailed in related Japanese Patent Application No. 2000-534831 on Feb. 9, 2010, 14 pages (including pending claims).
Japan Patent Office, "Decision of Refusal" mailed in related Japanese Patent Application No. 2003-555142 on Jun. 9, 2009. 7 pages (including pending claims).
Japan Patent Office, "Notification of Reasons for Refusal" mailed in related Japanese Patent Application No. 2003-555142 on Sep. 2, 2008, 12 pages (including pending claims).
Japan Patent Office, "Notification of Reasons for Refusal and Order" mailed in related Japanese Patent Application No. 2009-244069 on Jun. 29, 2010, 23 pages (including pending claims).
Japan Patent Office, "Notification of Reasons for Refusal" mailed in related Japanese Patent Application No. 2009-244176 on May 25, 2010, 8 pages (including pending claims).
PCT, "Notification of Transmittal of the International Search Report, or the Declaration", mailed in corresponding International Application No. PCT/US99/04053 on Feb. 25, 1999, 6 pages.
PCT, "Notification of Transmittal of the International Search Report and the Written Opinion of the International Searching Authority, or the Declaration" mailed in corresponding International Application No. PCT/US06/01067 on Jul. 3, 2008, 12 pages.
PCT, "Notification of Transmittal of the International Search Report and the Written Opinion" mailed in International Application No. PCT/US02/41151 on Dec. 19, 2002, 10 pages.
PCT, International Preliminary Examination Report for International Application No. PCT/US99/04053 mailed on Jul. 3, 2000.
PCT, "Written Opinion" mailed in International Application No. PCT/US99/04053 on Mar. 27, 2000.
USPTO, "Office Action" mailed in related U.S. Appl. No. 10/327,466 on Feb. 17, 2005, 11 pages.
USPTO, "Final Office Action" mailed in related U.S. Appl. No. 10/327,466 on Aug. 15, 2005, 17 pages.
USPTO, "Final Office Action" mailed in related U.S. Appl. No. 10/327,466 on Nov. 15, 2006, 10 pages.
USPTO, "Office Action" mailed in related U.S. Appl. No. 11/329,500 on May 27, 2008, 33 pages.
USPTO, "Office Action" mailed in related U.S. Appl. No. 11/614,315 on Apr. 23, 2007, 15 pages.
USPTO, "Office Action" mailed in related U.S. Appl. No. 11/614,315 on Jun. 19, 2009, 48 pages.
USPTO, "Office Action" mailed in related U.S. Appl. No. 11/868,740 on Oct. 29, 2009, 16 pages.
USPTO, "Office Action" mailed in related U.S. Appl. No. 12/419,158 on Nov. 13, 2009, 13 pages.
USPTO, "Office Action" mailed in related U.S. Appl. No. 90/007,798 on Jun. 12, 2009, 57 pages.
USPTO, "Office Action" mailed in related U.S. Appl. No. 90/700,800 on Jul. 21, 2009, 57 pages.
USPTO, "Ex Parte Reexamination Advisory Action" mailed in related U.S. Appl. No. 90/007,800 on Sep. 10, 2009, 39 pages.
USPTO, "Notice of Intent to Issue Ex Parte Reexamination Certificate" mailed in related U.S. Appl. No. 90/007,798 on Sep. 3, 2009, 7 pages.
USPTO, "Order Granting Request for ExParte Reexamination" mailed in related Ex Parte U.S. Appl. No. 90/010,659 on Oct. 29, 2009, 12 pages.
USPTO, "Office Action", mailed in related Ex-Parte U.S. Appl. No. 90/010,659 on May 28, 2010, 32 pages.
USPTO "Request for Reexamination of U.S. Patent 6,590,656 B2" mailed in related U.S. Appl. No. 90/010,659 on Aug. 28, 2009, 11 pages.
USPTO, "Notice of Failure to Comply with Ex Parte Reexamination Request for Filing Requirements", mailed in related Ex Parte U.S. Appl. No. 90/010,659 on Sep. 10, 2009, 7 pages.
USPTO "Replacement Statement and Explanation Under 37 CFR § 1.501(1) and (2) Including a Claims Chart", served by mail by Michael J. Halbert on Sep. 21, 2009, in re related Ex Parte U.S. Appl. No. 90/010,659, 39 pages.
USPTO, "Notice of Reexamination Request Filing Date" and "Notice of Assignment of Reexamination Request", mailed in related Ex Parte U.S. Appl. No. 90/010,659 on Sep. 23, 2009, 2 pages.
USPTO, "Order Granting Request for Ex Parte Reexamination", mailed in related Ex Parte U.S. Appl. No. 90/010,659 on Oct. 29, 2009, 12 pages.
Acosta, R.E. et al., "Method for Measuring Membrane Thickness", IBM Technical Disclosure Bulletin, Apr. 1, 1985, p. 6609.
Arimoto, H., "Precise Line-and-Space Monitoring Results by Ellipsometry", Jpn. J. Appl. Phys. vol. 36, Part 2, No. 2A, pp. L173-L175 (Feb. 1997).
Aspnes, "Effects of component optical activity in data reduction and calibration of rotating-analyzer ellipsometers", Journal of Optical Society of America, vol. 64, No. 6, Jun. 1974, 7 pages.
Azzam, "Ellipsometry", Handbook of Optics, vol. 2, Devices, Measurements and Properties, Second Edition, Optical Society of America, McGraw Hill, Inc., 1995, 27 pages.
Badami, D. et al., "End-Point Detection Method for Mask Etching", IBM Technical Disclosure Bulletin, Jan. 1, 1985, 1 page.

Baker, L.R., "Polarization micro-metrology", Polarization Considerations for Optical Systems II, Proceedings SPIE—The International Society for Optical Engineering, vol. 1166, Aug. 9-11, 1989, San Diego, CA, pp. 188-197.

Bakoglu, H.B., et al., "Small Lightweight High Resolution Optical Sensor for Specular Reflectors", IBM Technical Disclosure Bulletin, Jun. 1, 1985, 2 pages.

Baldauf, L., et al. "Infrared Laser Pattern Generation of Solder Masks", IBM Technical Disclosure Bulletin, Dec. 1986, 2 pages.

Bard, S.L.,"E-Beam Testing of Printed Circuit Conductors", IBM Technical Disclosure Bulletin, IBM Technical Disclosure Bulletin, Aug. 1, 1986, 2 pages.

Barrager, S.M., et al., "Measuring Torsional Properties of Tubes", IBM Technical Disclosure Bulletin, Aug. 1969, 2 pages.

Batchelder, J.S., et al., "Measurement of Trench Depth During Etching Process", IBM Technical Disclosure Bulletin, Dec. 1990, 2 pages.

Batchelder, J.S., "Luminescence Measurement of Photoresist Thickness", IBM Technical Disclosure Bulletin, Nov. 1986, 1 page.

Batchelder, J.S., "Patterned Wafer Scanner", IBM Technical Disclosure Bulletin, Mar. 1, 1985, 1 page.

Batchelder, J.S., "Scanning Optics", IBM Technical Disclosure Bulletin, Feb. 1986, 1 page.

Batchelder, J.S., et al, "Wafer Contamination and Defect Size Measurement Using Temporal Reflectance Variation From a Spatially Patterned Excitation", IBM Technical Disclosure Bulletin, Jun. 1, 1985, 2 pages.

Bates, K.A., et al., "Astigmatic Length Reduction for Diode Lasers in Optical Data", IBM Technical Disclosure Bulletin, Mar. 1994, 1 page.

Beach, D.B., et al., "Low Leakage, Temperature Invariant, High Dielectric Constant Films, using Multilayered Sol-Gel Fabrication", IBM Technical Disclosure Bulletin, Sep. 1994, 3 pages.

Beha, J.G., et al., "Contactless Resistance Measurement by a Combination of E-beam and Photoemission Methods", IBM Technical Disclosure Bulletin, Jan. 1987, 2 pages.

Bennett, W.O., "Semiconductor Laser Diode Array Used in Thin Film Redistribution", IBM Technical Disclosure Bulletin, May 1, 1985, 2 pages.

Bhattacharya, S., et al., "Measurement Method for Solder Creep Resolution of Less Than 5 Microns", IBM Technical Disclosure Bulletin, Apr. 1978, 2 pages.

Bickford, H.R., et al., "Enhanced Planarity Dielectric Process for Thin Film Fabrication", IBM Technical Disclosure Bulletin, Nov. 1994, 2 pages.

Blayo, N. et al., "New Applications of Ellipsometry for Materials Characterization and VLSI Device Process Control" Diagnostic Techniques for Semiconductor Materials and Devices, The Electrochemical Society Proceedings vol. 94-33, Editors Schroder et al., 1994, pp. 207-216.

Blayo N. et al., "Ultraviolet-visible ellipsometry for process control during the etching of submicrometer features", J. Opt. Soc. Am A, vol. 12, No. 3, Mar. 1995, pp. 591-599.

Block, T.R., et al., "Spot Centering for a Semiconductor Laser", IBM Technical Disclosure Bulletin, Jun. 1986, 1 page.

Bobroff, N., et al., "Optical System to Correct Nonlinearity in Heterodyne Interferometers", IBM Technical Disclosure Bulletin, Aug. 1990, 3 pages.

Bohlen, H., et al., "Optical System with Multiple Beams for Excimer Laser Ablation", IBM Technical Disclosure Bulletin, Oct. 1994, 1 page.

Bondesen, W., "Laser End-Point-Detection System", IBM Technical Disclosure Bulletin, Dec. 1, 1985, 2 pages.

Boyd, F.E., et al., "Automatic Ellipsometer System", IBM Technical Disclosure Bulletin, Apr. 1977, 3 pages.

Brady, M.J., et al., "Contactless Substrate Temperature Measurement by Laser Interferometry", IBM Technical Disclosure Bulletin, Apr. 1987, 2 pages.

Brady, M.J., et al, "Process for Sub-Micron Circuit Fabrication", IBM Technical Disclosure Bulletin, Jun. 1, 1985, 1 page.

Brennan, S., et al., "Nondestructive Characterization of Ultrathin Carbon Films", IBM Technical Disclosure Bulletin, Apr. 1990, 3 pages.

Briska, M., et al., "Ellipsometric Method of Measuring the Height of Steps in Wafer Surfaces", IBM Technical Disclosure Bulletin, Aug. 1978, 2 pages.

Briska, M., et al., "Laser-Induced Mass Spectrometry With High Lateral Resolution", IBM Technical Disclosure Bulletin, Mar. 1987, 2 pages.

Brooks, W.W., et al., "Measuring Critical Slider Location Using Optical Flat", IBM Technical Disclosure Bulletin, Mar. 1991, 2 pages.

Bross, A., et al., "Optoelectronic Assembly Utilizing Liquid Crystal Polymer", IBM Technical Disclosure Bulletin, Jan. 1994, 2 pages.

Brown, M,E., et al., "Positioning Mechanism for Electron Beam Drilling", IBM Technical Disclosure Bulletin, May 1991, 2 pages.

Brunsvold, W.R. et al., "Improved Optical MLR Underlayer", IBM Technical Disclosure Bulletin, Jan. 1, 1985, 2 pages.

Brusic, V.A., et al,, "Metallic Overlayer for CoP Protection in Thin Film Disks", IBM Technical Disclosure Bulletin, Aug. 1989, 2 pages.

Bucchignano, J.J., et al., "Mixed E-Beam + Optical Lithographic Patterning Process", IBM Technical Disclosure Bulletin, Feb. 1995, 2 pages.

Call, D.E., et al., "Laser-Feedback Noise Reduction by Optical Path Length Selection", IBM Technical Disclosure Bulletin, May 1990, 1 page.

Campbell, G.M., et al., "Pattern Offset Correction by Reverse Reflection", IBM Technical Disclosure Bulletin, Jan. 1, 1985, 2 pages.

Capezzuto, M., et al., "Surface Finish Apparatus for Thin Film Disks", IBM Technical Disclosure Bulletin, Jan. 1994, 1 page.

Carden, G., et al., "Nested Dual Cam Optical Transmitter", IBM Technical Disclosure Bulletin, Feb. 1994, 2 pages.

Carnel, R., et al., "Ellipsometer Measurement of Thin Films", IBM Technical Disclosure Bulletin, Feb. 1971, 2 pages.

Case, W., et al., "Measuring Thickness of Epitaxial Layer", IBM Technical Disclosure Bulletin, Jul. 1, 1985, 2 pages.

Cato, R.T., "Ultra Reliable Non-Contact Laser Wand with no Moving Parts", IBM Technical Disclosure Bulletin, May 1990, 2 pages.

Cerniglia, T.J., et al., "Polarization Enhancement Feature on 4dm Vision Engineering Dynoscope", IBM Technical Disclosure Bulletin, Jan. 1, 1985, 1 page.

Chang, D.C., "Control System for Electro Optic Digital Light Deflector", IBM Technical Disclosure Bulletin, Dec. 1967, 2 pages.

Chang, T.P., et al., "Electron Beam Inspection Method for Ceramic Greensheets", IBM Technical Disclosure Bulletin, Feb. 1986, 1 page.

Chang, T.P., et al., "Non-Contacting Techniques for Sample Charging in Electron Beam Inspection or Testing Apparatus", IBM Technical Disclosure Bulletin, May 1991, 3 pages.

Chapin, F,W., et al., "Method of Making a Lower-Cost Low-Dielectric Constant Material", IBM Technical Disclosure Bulletin, Feb. 1994, 2 pages.

Chappelow, R.E., "Extending the Utility of Current Generation Scanning Photolithographic Tools", IBM Technical Disclosure Bulletin, Mar. 1986, 2 pages.

Charsky, R.S., et al., "Advanced Diffraction Pattern Analysis Algorithm", IBM Technical Disclosure Bulletin, Jun. 1977, 5 pages.

Chastang, J.C., et al., "Automated Surface Profile and Film Thickness Analyzer", IBM Technical Disclosure Bulletin, May 1987, 4 pages.

Chastang, J.C., et al., "Horizontal Sample Attachment for Vertical Sample Ellipsometer", IBM Technical Disclosure Bulletin, Jun. 1982, 4 pages.

Chen, M., et al., "Fabrication of Anisotropic Particulate Media for Magnetic and Optical Storage Applications", IBM Technical Disclosure Bulletin, Apr. 1985, 1 page.

Chen, L., et al., "Laser Induced Silicon Etching With Nano-second Pulsed Laser At/below Visible Wavelength", IBM Technical Disclosure Bulletin, Jan. 1986, 2 pages.

Chen, L., et al., "Localized Emission Signal Collection Technique for Process End-Point Detection", IBM Technical Disclosure Bulletin, Mar. 1991, 1 page.

Chiaiese, V.C., et al., "Laser Sizing of Green MLC Laminates", IBM Technical Disclosure Bulletin, Apr. 1982, 2 pages.

Chiu, G.L.T., "Defocused E-beam for Testing", IBM Technical Disclosure Bulletin, Mar. 1986, 2 pages.

Chiu, S.L., "Structure for Inspection of Voids in Dielectric Thin Films", IBM Technical Disclosure Bulletin, Mar. 1995, 2 pages.

Christmas, H.F., et al., "Non-Contact Method for Measuring Plating Thickness", IBM Technical Disclosure Bulletin, Jun. 1994, 2 pages.

Chuang, T.J., "Laser Induced Etching of Copper and Chromium-copper by Fluorine-Containing Gases", IBM Technical Disclosure Bulletin, Mar. 1, 1985, n251, 1 page.

Chipman, "Polarimetry", Handbook of Optics, vol. 2, Devices, Measurements and Properties, Second Edition, Optical Society of America, McGraw Hill, Inc., 1995, 37 pages.

Coates et al., "Ultraviolet-Visible Microspectrophotometer System for Small-Spot Measurement and Characterization of Thin Films", SPIE vol. 1261 Integrated Circuit Metrology, Inspection, and Process Control IV (1990) p. 492-494.

Collins, "Automatic rotating element ellipsometers: Calibration, operation, and real-time applications", Rev. Sci Instrum. 61, (8), Aug. 1990, 33 pages.

Crandall and Chipman, "Polarization aberrations of crossed folding mirrors", SPIE, vol. 2537, (1995) 10 pages.

Clitheroe, A.M., et al., "CRT Beam Spot Contour Measurement", IBM Technical Disclosure Bulletin, Jul. 1, 1985, 2 pages.

Coane, P.J., et al., "Voltage Contrast Registration Marks for Election Beam Lithography", IBM Technical Disclosure Bulletin, Jun. 1, 1985, 2 pages.

Cohen, D.K., et al., "Beam Multiplication for Erasing Optical Phase-Change Recording", IBM Technical Disclosure Bulletin, Jan. 1986, 1 page.

Cohen, S.A., et al., "High Resolution Depth Profiling of Thin Oxide Nitride Oxide (ONO) Structures", IBM Technical Disclosure Bulletin, Aug. 1991, 2 pages.

Coombes, C.R., et al, "Measurement of CRT Beam Current", IBM Technical Disclosure Bulletin, Nov. 1, 1982, 2 pages.

Copel, M., et al., "Application of Sheet Resistance Probe to Control of Chemical Vapor Deposition Process", IBM Technical Disclosure Bulletin, Feb. 1991, 2 pages.

Corle T.R., "A broadband UV small spot spectroscopic ellipsometer", SPIE Microlithography, 1995, pp. 1-12.

Coufal, H., et al., "Nondestructive and Noncontact Measurement of Air Gap Thickness Between Stationary or Moving Opaque Films", IBM Technical Disclosure Bulletin, Apr. 1, 1985, 2 pages.

Coulombe et al., "Ellipsometric-Scatterometry for sub-0.1 µm CD Measurements", Center for High Technology Materials, University of New Mexico, SPIE vol. 3332, pp. 283-292 (1998).

Coyard, M., "Thickness and Refractive Index Determination for Thin Films", IBM Technical Disclosure Bulletin, Oct. 1983, 2 pages.

Criscimagna, T.N., et al., "Sensor Sighting for Interactive Triangulation", IBM Technical Disclosure Bulletin, Jun. 1, 1985, 1 page.

Crowder, M.S., et al., "Post-Deposition Surface Processing of Thin-Film Disks", IBM Technical Disclosure Bulletin, Mar. 1993, 1 page.

Cuomo, J.J., et al., "Infrared Laser Interferometric Measurement of Substrate Temperature and Film Growth Rates", IBM Technical Disclosure Bulletin, Jul. 1990, 3 pages.

Curtis, H.W., et al., "Contactless Electrical Equivalent Oxide Thickness Measurement", IBM Technical Disclosure Bulletin, Mar. 1987, 2 pages.

de Fresart, E., et al., "Germanium Concentration Depth Profiles of Silicon-Germanium Alloys Using Rie/Ellipsometry", IBM Technical. Disclosure Bulletin, Jun. 1991, 1 page.

De Smet, D.J., "Ellipsometry of anisotropic substrates: Re-examination of a special case", J. Appl. Phys. 76 (5), Sep. 1, 1994, pp. 2571-2574.

Delecki, J.J., "Small Device Capacitance Measurement Using a Scanning Electron Microscope", IBM Technical Disclosure Bulletin, Apr. 1986, 2 pages.

Deshpande, A.P., et al., "Use of Reflectivity Measurement in Infrared to Access in N-58 Ceramic Wafers", IBM Technical Disclosure Bulletin, Dec. 1995, 2 pages.

Despont, M., et al., "Fabrication of Vertically Aligned Apertures for E-Beam Microcolumn Application", IBM Technical Disclosure Bulletin, Dec. 1994, 2 pages.

Dill, F.H., et al., "Ellipsometry with Pulsed Tunable Laser Sources", IBM Technical Disclosure Bulletin, Sep. 1976, 2 pages.

Doany, F., at al., "Automated Laser Driver Laser-Planarisation Process", IBM Technical Disclosure Bulletin, Oct. 1994, 2 pages.

Doany, F.E., et al., "Continuously Variable Optical Defocus System for Laser Ablation Edge Profile Control", IBM Technical Disclosure Bulletin, May 1995, 1 page.

Doany, F., et al., "Laser Ablation Wall Angle Enhancement", IBM Technical Disclosure Bulletin, Aug. 1994, 1 page.

Domenicucci, A.G., et al., "Method for Early Determination of Leakages in Polysilicon Emitter Transistor Fabrication Using an Electron Beam", IBM Technical Disclosure Bulletin, Jan. 1, 1986, 2 pages.

Druschel, W.O., et al., "Laser Individual Chip Rework System", IBM Technical Disclosure Bulletin, May 1, 1985, 1 page.

Druschke, F., et al., "Laser Ablation of Polymer Thin Films", IBM Technical Disclosure Bulletin, Jan. 1995, 2 pages.

Ehrenberg, S.G., et al., "Magnetic, Self-Aligned Laser and Screening Mask", IBM Technical Disclosure Bulletin, Jun. 1991, 2 pages.

Elsner, G., et al., "Optical Line Width Measurement in the Submicron Range", IBM Technical Disclosure Bulletin, Jun. 1990, 3 pages.

Euen, W., et al., "Quality Determination of Dielectric Layers", IBM Technical Disclosure Bulletin, Feb. 1994, 2 pages.

Fan, L.S., et al., "Batch-Fabricated Magnetic Microactuators", IBM Technical Disclosure Bulletin, Sep. 1994, 2 pages.

Fan, L.S., et al., "Integrated Notched Pin Joint and other Multilayer Structures with High-Aspect Ratio Gaps and Method of Fabrication Thereof", IBM Technical Disclosure Bulletin, Apr. 1995, 3 pages.

Fan, B., et al., "Laser Micro-Fabrication of Waveguide Devices", IBM Technical Disclosure Bulletin, Apr. 1989, 3 pages.

Feger, C., et al., "Laser Inteferometric Monitor of Polymer Thin Film Properties During Device Fabrication", IBM Technical Disclosure Bulletin, Oct. 1986, 2 pages.

Feig, E., et al., "Alignment Algorithm for Determining Via Centers of Substrate Layers", IBM Technical Disclosure Bulletin, Apr. 1994, 2 pages.

Fertile, F.F., et al., "Optical Alignment Method to Insure Accurate Sizing of Patterned Substrates", IBM Technical Disclosure Bulletin, Jun. 1990, 1 page.

Fetzer, P., et al., "Multiple Exposer Calibration Curves for Optical Measurement Tools", IBM Technical Disclosure Bulletin, Oct. 1990, 2 pages.

Finnes, S., "Device/Process for the Characterization on a Semiconductor Lithography Tool", IBM Technical Disclosure Bulletin, Apr. 1, 1985, n252, 1 page.

Forouhi, A.R. et al. "Optical dispersion relations for amorphous semiconductors and amorphous dielectrics", Physical Review B, vol. 34, No. 10, Nov. 15, 1986, pp. 7018-7026.

Forouhi, A.R. et al. "Optical properties of crystalline semiconductors and dielectrics", Physical Review B, vol. 38, No. 3, Jul. 15, 1988, pp. 1865-1873.

Fredericks, E.C., et al., "Improved Method of Exposing Resists With Lasers", IBM Technical Disclosure Bulletin, Nov. 1986, 2 pages.

Freisitzer, N., et al., "Automatic Location and Recording System for Semiconductor Chip Sites", IBM Technical Disclosure Bulletin, Jun. 1, 1985, 2 pages.

Frosch, A., et al., "High-Precision Laser Scanning Microscope", IBM Technical Disclosure Bulletin, Mar. 1986, 2 pages.

Frosch, A., et al., "Triple-Prism Optical Phase Shifter", IBM Technical Disclosure Bulletin, Mar. 1, 1985, 2 pages.

Gaspar, S.M., et al., "Applications of Light Scatter for Microelectronics Manufacturing", Surface Roughness and Scattering: First Topical Meeting, Jun. 1-3, 1992 (Optical Society of America, Washington, D.C., 1992) pp. 30-31.

Gaspar, S.M., et al., "Metrology of etched quartz and chrome embedded phase shift gratings using scatterometry", Proc. SPIE vol. 2439, Apr. 1995, pp. 479-494.

Gaylord, T.K. et al "Analysis and Applications of Optical Diffraction by Gratings", Proceedings of the IEEE, vol. 73, No. 5, May 1985, pp. 894-937.

Gehrtz, M., et al., "Suppression of Residual Amplitude Modulation in Laser Frequency Modulation Measurement Techniques", IBM Technical Disclosure Bulletin, Aug. 1, 1986, 2 pages.

Giapis, et al., "Use of Light Scattering in Characterizing Reactively Ion Etched Profiles", Submitted to J. Vac. Sci. Technol. Oct. 25, 1990, pp. 1-15.

Gillespie, S.J., "Linewidth Variation in E-Beam Technology", IBM Technical Disclosure Bulletin, Nov. 1, 1982, 2 pages.

Gillespie, S.J., "Submicron E-Beam Imaging Process", IBM Technical Disclosure Bulletin, Mar. 1987, 2 pages.

Gobran, F.S., et al., "Orthogonal Intersecting Light Beam Position Locater", IBM Technical Disclosure Bulletin, May 1986, 2 pages.

Goetz, W.E., et al., "Chip Identification Writer Optics", IBM Technical Disclosure Bulletin, Jan. 1, 1985, 3 pages.

Goldburt, E., et al., "Laser Scanner Using Single-Mode Fiber and Cholesteric Liquid Crystal", IBM Technical Disclosure Bulletin, Apr. 1986, 3 pages.

Golladay, S.D. et al., "Electron Beam Testing of Electronic Packages Using a Continuously Rotating Table", IBM Technical Disclosure Bulletin, Jan. 1, 1986, 1 page.

Goodman, D.S., et al., "Light Tunnel Illumination Apparatus", IBM Technical Disclosure Bulletin, Mar. 1, 1985, 2 pages.

Goodman, D.S., "Scanning Ring Illumination for Laser Processing", IBM Technical Disclosure Bulletin, Mar. 1987, 2 pages.

Goodman, D.S., "Tilted Vertical Illumination for Linear Detector Arrays", IBM Technical Disclosure Bulletin, Oct. 1, 1986, 2 pages.

Haelbich, R.P., "Apodization Technique for Achieving Uniform Illumination in Storage Ring X-Ray Lithography", IBM Technical Disclosure Bulletin, Mar. 1, 1985, 2 pages.

Hamahata, K., et al., "Optical Head", IBM Technical Disclosure Bulletin, Jan. 1995, 1 page.

Harder, C., "Wafer Discharging During Electron-Beam Exposure", IBM Technical Disclosure Bulletin, Apr. 1, 1985, 2 pages.

Hartstein, A.M., et al., "Non-Destructive Testing of MOSFET Oxides", IBM Technical Disclosure Bulletin, Nov. 1, 1985, 1 page.

Hauge, P.S., "Method of Characterizing Optical System that Depolarize Light", IBM Technical Disclosure Bulletin, Jun. 1991, 2 pages.

Hickman et al. "Use of Diffracted Light From Latent Images to Improve Lithography Control", SPIE vol. 1464 Integrated Circuit Metrology, and Process Control V (1991) p. 245-257.

Hoffmeister, W., et al., "Determination of the Phosphorous Content and the Layer Thickness of Phosphorous Silicate Glass Layers", IBM Technical Disclosure Bulletin, Sep. 1973, 2 pages.

Houser, D.E., et al., "Optical Square", IBM Technical Disclosure Bulletin, Feb. 1995, 2 pages.

Hovel, H.S., "Wafer Bonding with Diamond Like Carbon Films", IBM Technical Disclosure Bulletin, Jan. 1993, 1 page.

Huang, K., et al., "Free Space Zone Skew Optical Routing", IBM Technical Disclosure Bulletin, Jan. 1993, 3 pages.

Hume, E.C., et al., "Optimized Endpoint Exposure for Photoresist Development", IBM Technical Disclosure Bulletin, Feb. 1987, 2 pages.

Ibok E. et al "Optical characterization of amorphous and polycrystalline silicon films",., *Solid State Technology*, Aug. 1995, 4 pages.

Jaerisch, W., et al., "Compact High-Resolution Interferometer", IBM Technical Disclosure Bulletin, Mar. 1, 1985, 1 page.

Jaerisch, W., et al., "Double-Resolution Interferometer for Rough or Reflecting Surfaces", IBM Technical Disclosure Bulletin, Mar. 1, 1985, 2 pages.

Jaerisch, W., et al, "Inspecting Scattering Pattern Carriers With Enhanced Optical Contrast", IBM Technical Disclosure Bulletin, Feb. 1, 1985, 2 pages.

Jaerisch W., et al., "Integrated Micromechanical Light Scanner", IBM Technical Disclosure Bulletin, Mar. 1, 1985, 1 page.

Jakubowicz, A., "High Resolution Thermaography of Microelectronic Devices by Electron Beam Charging Dielectric Coatings", IBM Technical Disclosure Bulletin, Apr. 1993, 1 page.

Jakubowicz, A., et al., "Reliable Method of Catastrophic Optical Mirror Damage Identification in Semiconductor Laser Diodes", IBM Technical Disclosure Bulletin, Jun. 1994, 2 pages.

Jenkins, K.A., "Electron-Beam Activated Linewidth Measurement Test Site", IBM Technical Disclosure Bulletin, Jun. 1991, 2 pages.

Jipson, V.B., et al., "Multiple-beam Optical Heads", IBM Technical Disclosure Bulletin, Jan. 1986, 2 pages.

Johnson, A.O., et al., "Beam Deflection Measurement Tip", IBM Technical Disclosure Bulletin, Dec. 1995, 3 pages.

Johnson, G.W., "Light Diffuser With Controlled Divergence", IBM Technical Disclosure Bulletin, Jun. 1, 1986, 2 pages.

Juetz, J., et al., "Spectral Range Sensing Using Dynamic Chromatic Aberration", IBM Technical Disclosure Bulletin, Feb. 1, 1985, 2 pages.

Kallmeyer, M., et al., "Electro-Optical Line Measurement", IBM Technical Disclosure Bulletin, Jun. 1990, 2 pages.

Kallmeyer, M., et al., "Laser Scanning Microscope With Micromechanical Scale", IBM Technical Disclosure Bulletin, Mar. 1990, 2 pages.

Kaplan, L., "Technique for E-Beam Exposure Tool Evaluation", IBM Technical Disclosure Bulletin, May 1991, 2 pages.

Keyes, R.W., "Optical Logic with QCSE Devices and Polarized Light", IBM Technical Disclosure Bulletin, Jul. 1994, 3 pages.

Kiefer, E., et al., "Miniaturized Ellipsometer", IBM Technical Disclosure Bulletin, Mar. 1994, 1 page.

Kiefer, E., et al., "Miniaturized Multi-Angle Ellipsometer", IBM Technical Disclosure Bulletin, Mar. 1994, 1 page.

Kin, C.C., et al, "Non-Contact Height Monitor", IBM Technical Disclosure Bulletin, Oct. 1, 1985, 2 pages.

Kirby, D.P., "Method for Eliminating Interference Fringes for Thin Film Infrared Measurements", IBM Technical Disclosure Bulletin, Mar. 1, 1985, 2 pages.

Krakow, W., et al., "Laser System for Metallurgical Diagnostics", IBM Technical Disclosure Bulletin, Oct. 1, 1985, 2 pages.

Krukar, R.H., et al., "Using Scattered Light Modeling for Semiconductor Critical Dimension Metrology and Calibration", Proc. SPIE vol. 1926, Apr. 1993, pp. 60-71.

Lang, R.W., et al., "Active Alignment and Measuring Tool for Fiber-Optic Laser Subassemblies", IBM Technical Disclosure Bulletin, Sep. 1990, 2 pages.

Lankard, J.R., "Optical Fiber Laser Beam Distributor", IBM Technical Disclosure Bulletin, Sep. 1, 1985, 2 pages.

Latta, M.A., "Material Patterning and Removal by Holographically Imaged Laser Radiation", IBM Technical Disclosure Bulletin, May 1, 1985, 2 pages.

Li, C.S., et al., "Fault Detection and Isolation in Optical Transmission Systems using Optical Amplifiers", IBM Technical Disclosure Bulletin, May 1995, 3 pages.

Li, L., "Formulation and Comparison of Two Recursive Matrix Algorithms for Modeling Layered Diffraction Gratings", J. Opt. Soc. Am. A, vol. 13, No. 5, pp. 1024-1035 (May 1996).

Li L. et al.,"Convergence of the coupled-wave method for metallic lamellar diffraction gratings", *Journal of the Optical Society of America A*, vol. 10, No. 6, Jun. 1993, pp. 1184-1188.

Li, L. Multilayer modal method for diffraction gratings of arbitrary profile, depth, and permitivity, *Journal of the Optical Society of America A*, vol. 10, No. 12, Dec. 1993, pp. 2581-2591.

Li, L. "A model analysis of lamelar diffraction gratings in a conical mounting", *Journal of Modern Optics*, vol. 40, No. 4, 1993, pp. 553-573.

Lin, B.J., "Depth-Of-Focus Enhancement Using High Refractive Index Layer on the Imaging Layer", IBM Technical Disclosure Bulletin, Apr. 1, 1985, 2 pages.

LoDato, V.A., "Step Beamsplitter for Laser Beams", IBM Technical Disclosure Bulletin, Apr. 1986, 1 page.

Loughran, J.F., et al., "Technique of Characterizing Calibration Grids in E-Beam Lithography Tools", IBM Technical Disclosure Bulletin, Nov. 1, 1982, 3 pages.

Loy, M.M., et al., "Optical Microscopy Using Second-Harmonic Generation", IBM Technical Disclosure Bulletin, May 1987, 2 pages.

Lueck, P., et al., "Structuring of Laminated Cu-Polyimide Films via Laser Ablation", IBM Technical Disclosure Bulletin, Aug. 1994, 2 pages.

Luecke, F., "Laser Diode Angular Orientation Sensing Technique", IBM Technical Disclosure Bulletin, May 1990, 2 pages.

Luecke, F.S., "Laser Beam Size Measurement Technique", IBM Technical Disclosure Bulletin, Apr. 1, 1985, 1 page.

Luecke, F., "Polarization Splitting Prism", IBM Technical Disclosure Bulletin, Jun. 1990, 2 pages.

Lukianoff, G.V., "Microscopic Height Measurement System", IBM Technical Disclosure Bulletin, Oct. 1, 1985, 1 page.

Mahlbacher, J., et al., "Combined Optical Inspection and Electrical Measurement Systein", IBM Technical Disclosure Bulletin, Oct. 1994, 1 page.

Maldonado, J.R., et al., "End-Point Detection Technique Utilizing Changes in Birefringence", IBM Technical Disclosure Bulletin, Jan. 1991, 1 page.

Manthei, L. W., et al., "Automated Multiple Angle of Incidence Ellipsometer System", IBM Technical Disclosure Bulletin, Feb. 1990, 3 pages.

Marple, W.P., et al., "Edge-Detection Circuit", IBM Technical Disclosure Bulletin, Mar. 1, 1986, 2 pages.

McClelland, G.M., et al., "Small Bit Size Using Triboattractive Contact Slider of High Refractive Index", IBM Technical Disclosure Bulletin, Feb. 1994, 1 page.

McNeil, J.R., et al., "Optical Scatterometry", Encyclopedia of Materials Characterization, Surfaces, Interfaces, Thin Films, Editors C. Richard Bundle et al., Chapter 12.2, 1992, pp. 711-722.

McNeil, J.R. et al., "Scatterometry Applied to Microelectronics Processing—Part 1", Solid State Technology, Mar. 1993, 3 pages.

McNeil, J.R. et al., "Scatterometry Applied to Microelectronics Processing—Part 2", Solid State Technology, Apr. 1993, pp. 53-56.

Meeks, S.W., et al., "Method and Apparatus for Simultaneously Measuring Wear and Roughness on Thin Film Disks", IBM Technical Disclosure Bulletin, Apr. 1994, 2 pages.

Menzel, E., "Electron Beam Chopping System Without Chopping Degradation", IBM Technical Disclosure Bulletin, May 1, 1985, n253, 2 pages.

Mery, H.E., et al., "Digital Velocity From Two-Phase Optical Encoder", IBM Technical Disclosure Bulletin, Jun. 1991, 3 pages.

Mills. D. W. et al., "Spectral ellipsometry on patterned wafers", *SPIE's Microelectronic Manufacturing: Process, Equipment, and Materials Control in Integrated Circuit Manufacturing, Spie* vol. 2637, Austin (USA), 1995.

Mixon, W.E., "Optoelectronic Joystick Controller", IBM Technical Disclosure Bulletin, Jan. 1, 1985, 1 page.

Moerner, W.E., "Method and Device for Staircase Scanning of a Light Beam", IBM Technical Disclosure Bulletin, Dec. 1, 1985, 2 pages.

Moharam, M.G., "Coupled-Wave Analysis of Two-Dimensional Dielectric Gratings", Proc. SPIE, vol. 883, Holographics Optics: Design and Applications, pp. 8-11 (1988).

Moharam, M.G. et al., "Formulation for Stable and Efficient Implementation of the Rigorous Coupled-Wave Analysis of Binary Gratings", J. Opt. Soc. Am. A, vol. 12, pp. 1068-1076 (May 1995).

Moharam, M.G. et al "Rigorous coupled-wave analysis of planar-grating diffraction", *J. Opt. Soc. Am.*, vol. 71, No. 7, Jul. 1981, pp. 881-918.

Moharam, M.G. et al. "Stable implementation of the rigorous coupled-wave analysis for surface-relief gratings: enhanced transmittance matrix approach", *J. Opt. Soc. Am. A*, vol. 12, No. 5, May 1995, pp. 1077-1086.

Moore, R.D., et al., "Electron Beam Measurement With On-Line Calibration", IBM Technical Disclosure Bulletin, Jun. 1979, 2 pages.

Morrissey, J.M., et al., "Superposition of Voltage Contrast on Optical Image", IBM Technical Disclosure Bulletin, Jan. 1, 1985, 1 page.

Moylan, C.R., "Integrated Optical Storage Medium and Substrate", IBM Technical Disclosure Bulletin, Jun. 1994, 2 pages.

Murnane, M.R., et al., "Scatterometry for 0.24 µm-0.70 µm developed photoresist metrology", SPIE vol. 2439, May 1995, pp. 427-436.

Murnane, M.R., et al., "Subwavelength photoresist grating metrology using scatterometry", SPIE vol. 2532, Sep. 1995, pp. 251-261.

Murnane, M.R. et al., "Developed Photoresist Metrology Using Scatterometry", Center for High Technology Materials, University of New Mexico, SPIE vol. 2196, pp. 47-59 (Mar. 1994).

Nagda, J.M., et al., "Skew Detection for Linear Scanner", IBM Technical Disclosure Bulletin, Nov. 1, 1982, 1 page.

Nahata, P., et al., "Method to Detect the Presence or Absence of Laminated Thin Film in Silicon Wafer Fabrication", IBM Technical Disclosure Bulletin, Jun. 1994, 2 pages.

Novotny, V.J., "Ultrafast Ellipsometric Mapping of Thin Films", IBM Technical Disclosure Bulletin, Feb. 1994, 2 pages.

O'Brien, K.L., et al., "Electron Beam Inspectable Glass Mask", IBM Technical Disclosure Bulletin, May 1, 1985, 1 page.

Oehrlein, G., "Plasma Process Monitoring by Ellipsometry With Single Port Optical Access", IBM Technical Disclosure Bulletin, Jun. 1991, 2 pages.

Oehrlein, G.S., "Method for Determining Thickness of Polymer Contamination on Silicon After CF4/H2", IBM Technical Disclosure Bulletin, Aug. 1985, 1 page.

Ong, H.L., "Electrically Controlled Linear, Left-Circular, and Right-Circular Polarized Light Device", IBM Technical Disclosure Bulletin, Jul. 1991, 1 page.

Peck, R.C., "Laser Target Site Locator for Photoresist Development End-point Detect", IBM Technical Disclosure Bulletin, Oct. 1986, 2 pages.

Pfeiffer, H.C., et al., "Electron Beam Apparatus Having Auto-Centering Dynamic Focus", IBM Technical Disclosure Bulletin, Jan. 1, 1986, 2 pages.

Pforr R., et al., "In-Process Image Detecting Technique for Determination of Overlay, and Image Quality for ASM-L Wafer Stepper", *SPIE* vol. 1674 *Optical/Laser Microlithography V* (1992) pp. 594-608.

Pritt, M.D., "Algorithm for Two-Dimensional Phase Unwrapping Using Fast Fourier Transforms", IBM Technical Disclosure Bulletin, Mar. 1994, 3 pages.

Ray, M., "Angle of Incidence Calibration With a Tapered Film for Ellipsometers", IBM Technical Disclosure Bulletin, Nov. 1989, 3 pages.

Raymond, C.J., et al., "Multi-parameter process metrology using scatterometry", SPIE vol. 2638, Aug. 1995, pp. 84-93.

Raymond, C.J. et al "Metrology of subwavelength photoresist gratings using optical scatterometry", *J. Vac. Sci. Technol. B*, vol. 13, No. 4, Jul./Aug. 1995, pp. 1484-1495.

Rittle, J., et al., "Fiber-Optic Connector Interface Scheme that Provides for Worldwide Class I Laser Certification", IBM Technical Disclosure Bulletin, Jan. 1994, 1 page.

Ruppert, W., "Optical Scanning Head with Homogeneously Illuminated Image Plane", IBM Technical Disclosure Bulletin, Nov. 1, 1982, 2 pages.

Ruppert, W., "Optical Test Head with Flare Compensation", IBM Technical Disclosure Bulletin, Nov. 1, 1982, 1 page.

Safaraz, M.A., et al., "E-Beam Personalization for Quick Turn Around Ceramic Substrate Build", IBM Technical Disclosure Bulletin, Oct. 1994, 1 page.

Schrader, M., et al., "Electron Beam Microanalysis of Thin Alloy Films", IBM Technical Disclosure Bulletin, Mar. 1987, 1 page.

Schramm et al., "Algorithm Implementation and Techniques for Providing More Reliable Overlay Measurements and Better Tracking of the Shallow Trench Isolation (STI) Process", SPIE: Conference on Methrology, Inspection, and Process Control of Microlithography XIII, Mar. 1999, pp. 116-122.

Shott, F.A., "Piezoelectrically Aimed Laser", IBM Technical Disclosure Bulletin, Mar. 1991, 2 pages.

Singh, G.P., et al., "Apparatus and Technique for 3D Microscopy and Profilometry of Magnetic Recording Hard Disks using a Flying Slider", IBM Technical Disclosure Bulletin, Apr. 1994, 2 pages.

Smith, K.A., "Endpoint Detection by Change in Reflectance During Laser Repair of Thin Film Metallurgy", IBM Technical Disclosure Bulletin, Dec. 1986, 2 pages.

Sohail S. et al., "Scatterometry and the Simulation of Diffraction-Based Metrology", *Microlithography World*, Jul./Aug./Sep. 1993, pp. 5-16.

Spong, J.K., "Flying-Height Measurement Using Fiber-Optic Interferometry", IBM Technical Disclosure Bulletin, Nov. 1990, 2 pages.

Strand, T.C., "Color-Matched Filtering for White-Light Interferometry", IBM Technical Disclosure Bulletin, Feb. 1, 1985, 2 pages.

Toomey, T.J., "CO2 Laser-Scanning System using a Telecentric Relay System", IBM Technical Disclosure Bulletin, May 1987, 3 pages.

Tsukamoto, K., "Optical Inspection System", IBM Technical Disclosure Bulletin, May 1984, 2 pages.

Umezaki, H., "Thin Film Type Laminated Head", IBM Technical Disclosure Bulletin, Dec. 1994, 2 pages.

Van Vechten, J.A., "Scanning Electron Inspection System for Solder Pads", IBM Technical Disclosure Bulletin, Mar. 1, 1985, 2 pages.

Van Zeghbroeck, B.J., "Low-Threshold Vertical Emitting Laser", IBM Technical Disclosure Bulletin, Jun. 1990, 1 page.

Via, G., "Five-Degrees-Of-Freedom Stage for a Scanning Electron-Beam Microscope", IBM Technical Disclosure Bulletin, Aug. 1983, 2 pages.

von Gutfeld, R.J., "Large Area Laser-Enhanced Plating", IBM Technical Disclosure Bulletin, Mar. 1, 1985, 2 pages.

Warnecke, A.J., "Charge-Free Electron Beam Lithography", IBM Technical Disclosure Bulletin, Dec. 1, 1985, 2 pages.

Wells, O.C., "Optical Microscope Beyond the Detraction Limit", IBM Technical Disclosure Bulletin, Nov. 1, 1985, 3 pages.

Wickramasinghe, H.K., et al., "Scanning Polarizing Microscope", IBM Technical Disclosure Bulletin, IBM Technical Disclosure Bulletin, Mar. 1, 1987, 2 pages.

Yang, KH, "Optical Imaging Method for Investigation of Surface Irregularity", IBM Technical Disclosure Bulletin, Feb. 1, 1985, 1 page.

Yasuda and Aspens, "Optical-standard surfaces of single-crystal silicon for calibrating ellipsometers and reflectometers", Applied Optics, vol. 33, No. 31, Nov. 1994, Optical Society of America.

Zapka, W., "Damage-free Laser Ablation Removal of Organic Materials", IBM Technical Disclosure Bulletin, Oct. 1994, 1 page.

Ziger, D.H. et al., "Line size effects on ultraviolet reflectance spectra", *Opt. Eng.*, vol. 36, No. 1, Jan. 1997, pp. 243-250.

IBM Technical Disclosure Bulletin, "Spectroscopic Pitch Measurement Technique", vol. 32 No. 4B, Sep. 1989, pp. 391-392.

Diffraction: www.scienceworld.wolfram.com/physics/Diffraction.html, 2 pages, printed Jan. 27, 2004.

Physics 204 Laboratory 13 Diffraction Grating, www.physics.fsu.edu/courses/fall98/phy2049c/labs/L13.pdf, 7 pages.

"Spectroscopic Ellipsometry—A Technology Primer", KLA-Tencor, March 1991, 12 pages.

Extract of Meeting Schedule: "Abstract of Talks", 220/OSA Annual Meeting, Friday, Nov. 8, 1991, 1 page.

Azzam et al., "Polarization Chararacteristics of Scattered Radiation from a Diffraction Grating by Ellipsometry with Application to Surface Roughness," Physical Review B, vol. 5, No. 12, Jun. 15, 1972, pp. 4721-4729.

Aspnes, "Analysis of Semiconductor Materials and Structures by Spectroellipsometry," Proceedings of SPIE—The International Society for Optical Engineering, vol. 946, Mar. 14-15, 1988, Newport Beach, CA, 15 pages.

Bishop et al., "Grating line shape characterization using scatterometry," SPIE, vol. 1545, International Conference on the Application and Theory of Periodic Structures, 1991, pp. 64-73.

Brundle et al. (Series editors), "Encyclopedia of Materials Characterization," Materials Characterization Series. Surfaces, Interfaces, Thin Films. Copyrights 1992 by Butterworth-Heinemann. Whole book.

Butler et al., "Supervisory Run-to-Run Control of Polysilicon Gate Etch Using *In Situ* Ellipsometry," IEEE Transactions on Semiconductor Manufacturing, vol. 7, No. 2, May 1994, pp. 193-201.

Chipman, "Polarization Considerations for Optical Systems II," Proceedings SPIE—The International Society for Optical Engineering, vol. 1166, Aug. 9-11, 1989, San Diego, CA, 11 pages.

Glembocki et al., "Spectroscopic Characterization Techniques for Semiconductor Technology III," Proceedings of SPIE—The International Society for Optical Engineering, vol. 946, Mar. 14-15, 1988, Newport Beach, CA, 15 pages.

Haggans et al., "Effective-Medium Theory of Zeroth-Order Lamellar Gratings in Conical Mountings," J. Opt. Soc. Am. A, Oct. 19, 1993, vol. 10, No. 10, pp. 2217-2225.

Hatab et al., "Sixteen-megabit dynamic random access memory trench depth characterizing using two-dimensional diffraction analysis," J. Vac. Sci. Technol. B 13(2), Mar./Apr. 1995, pp. 174-182.

Haverlag et al., "In situ ellipsometry and reflectometry during etching of patterned surfaces: Experiments and simulations," J. Vac. Sci. Technol. B 10(6), Nov./Dec. 1992, pp. 2412-2418.

Heissmeier, "Calibration of a microlithographic fabrication process using non-destructive testing and rigorous electromagnetic theory," OPTIK, vol. 103, Issue 1, pp. 12-18. Published in Jul. 1996.

Jacobson et al., "Comparison of Optical Scatterometer and Profilometer Techniques for Characterizing Smooth Surfaces," SPIE vol. 1009, Surface Measurement and Characterization, 1988, pp. 77-80.

Jacobson et al., "Microstructure characterization by angle-resolved scatter and comparison to measurements made by other techniques," Applied Optics, vol. 31, No. 10, Apr. 1, 1992, pp. 1426-1435.

Kikuta et al., "Effective Medium Theory of Two-Dimensional Subwavelength Gratings in the Non-Quazi-Static limit," J. Opt. Soc. Am. A, vol. 15, No. 6, Jun. 1998, pp. 1577-1585.

Krukar, "A Methodology for the Use of Diffrated Scatter Analysis to Measure the Critical Dimensions of Periodic Structures", Dissertation, The University of New Mexico, May 1993, pp. 1-66.

Krukar et al., "Wafer examination and critical dimension estimation using scattered light," SPIE vol. 1661 (1992), pp. 323-332.

Lalanne et al., "High-Order Effective-Medium Theory of Subwavelength Gratings in Classical Mounting: Application to Volume Holograms," J. Opt. Soc. Am. A, vol. 15, No. 7, Jul. 1998, pp. 1843-1851.

Lalanne et al., "On the Effective Medium Theory of Subwavelength Periodic Structures," Journal of Modern Optics, 1996, vol. 43, No. 10, pp. 2063-2085.

Milner et al., "Stepper focus characterization using diffraction from latent images," J. Vac. Sci. Technol. B 11(4), Jul.Aug. 1993, pp. 1258-1266.

Minhas et al., "Ellipsometry scatterometry for the metrology of sub-0.1-µm-linewidth structures," Applied Optics, vol. 37, No. 22, Aug. 1, 1998, pp. 5112-5115.

Moharam et al., "Three-dimensional vector coupled-wave analysis of planar-grating diffraction," J. Opt. Soc. Am., vol. 73, No. 9, Sep. 1983, pp. 1105-1112.

Naqvi et al., "Etch depth estimation of large-period silicon gratings with multivariate calibration of rigorously simulated diffraction profiles," J. Opt. Soc. Am. A, vol. 11, No. 9, Sep. 1994, pp. 2485-2493.

Pai et al., "Analysis of dielectric gratings of arbitrary profiles and thicknesses," J. Opt. Soc. Am. A, vol. 8, No. 5, May 1991, pp. 755-762.

Peng et al., "Analysis of Periodic Thin-Film Structures with Rectangular Profiles," Optics Communications, vol. 10, No. 1, Jan. 1974, pp. 91-94.

Qu et al., "Polarization dependence of the electromagnetic field distribution across wavelength-sized relief grating surfaces," J. Opt. Soc. Am. A, vol. 10, No. 11, Nov. 1993, pp. 2317-2323.

Raymond et al., "Multiparameter grating metrology using optical scatterometry," J. Vac. Sci. Technol. B 15(2), Mar./Apr. 1997, pp. 361-368.

Schroder et al., "Diagnostic Techniques for Semiconductor Materials and Devices," The Electrochemical Society Proceedings vol. 94-33, pp. 207-216, total 8 pages, 1994.

Smet et al., "Ellipsometry of anisotropic substrates: Re-examination of a special case," J. Appl. Phys. 76 (5), Sep. 1, 1994, pp. 2571-2574.

Sohail et al., "A Simple Technique for Linewidth Measurement of Gratings on Photomasks," SPIE vol. 1261, Integrated Circuit Metrology, Inspection, and Process Control IV (1990), pp. 495-504.

Sohail et al., "Grating Parameter Estimation using Scatterometry," SPIE vol. 1992 Miniature and Micro-Optics and Micromechanics (1993), pp. 170-180.

Stover, "Optical Scattering—Measurement and Analysis", Copyrights 1995 by The Society of Photo-Optical Instmmentation Engineers. Whole book.

Tompkins et al., "Spectroscopic Ellipsometry and Reflectometry: A User's Guide," John Wiley & Sons, Inc., New York, 1999, 9 pages.

Wang et al., "Influence of semiconductor manufacturing process variation on device parameter measurement for angular scatterometry," SPIE Microlithography World 2006, 9 pages.

Wilson et al., "Methrology of etched quartz and chrome embedded phase shift gratings using scatterometry," SPIE vol. 2439, pp. 479-494, 1995.

Japanese Patent Office, "Notification of Reasons for Refusal," corresponding Japanese Patent Application No. 2000-534831, mailed on Sep. 16, 2008, 8 pages (including translation.).

JPO, Notification of Reasons for Refusal mailed in related Japanese patent application No. 2010-131079 on Nov. 30, 2010, 2 pages with pending claims.

EPO, Office Action mailed in related European patent application No. 04078145.2 on Dec. 22, 2010, 3 pages with pending claims.

\* cited by examiner

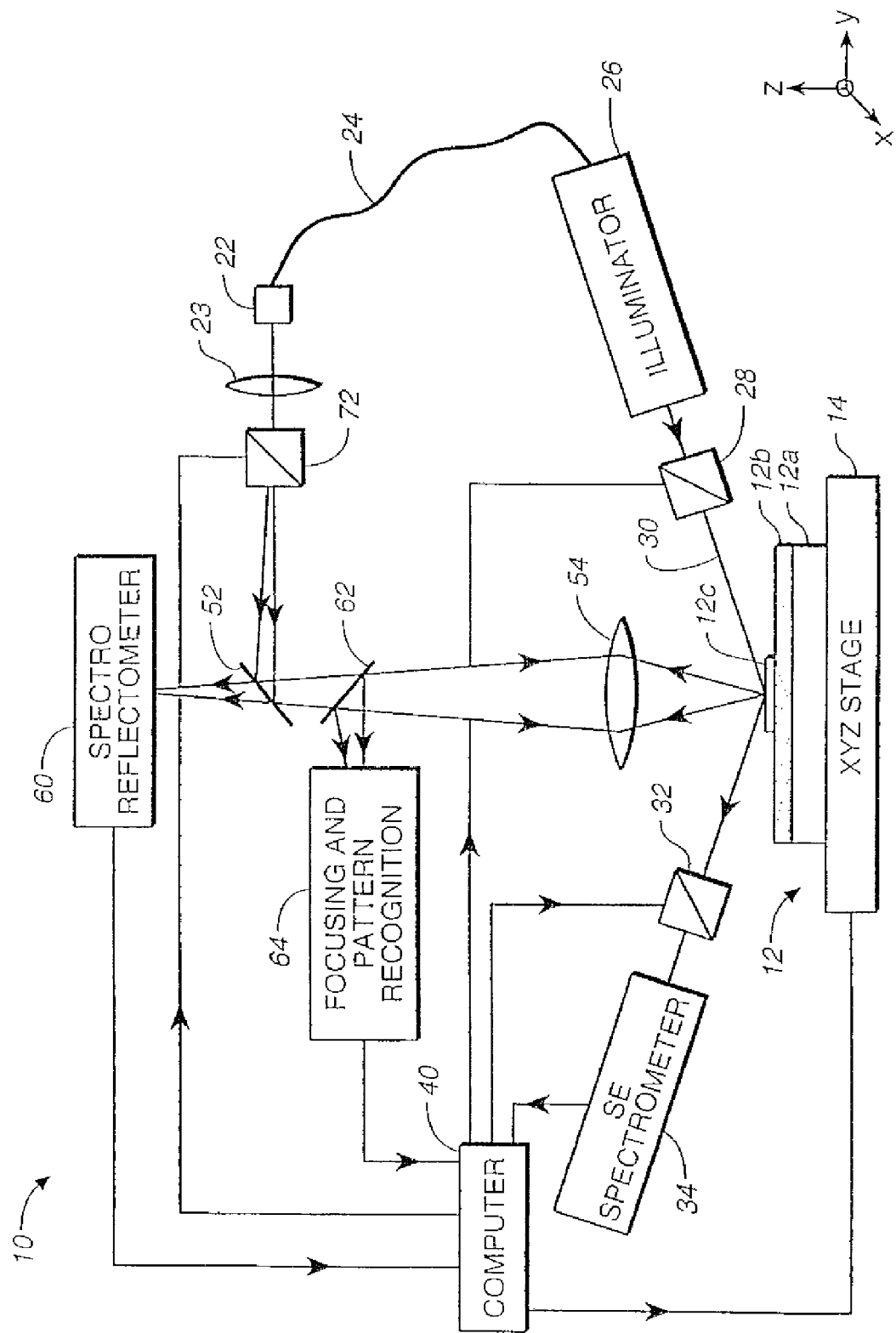
FIG._1A

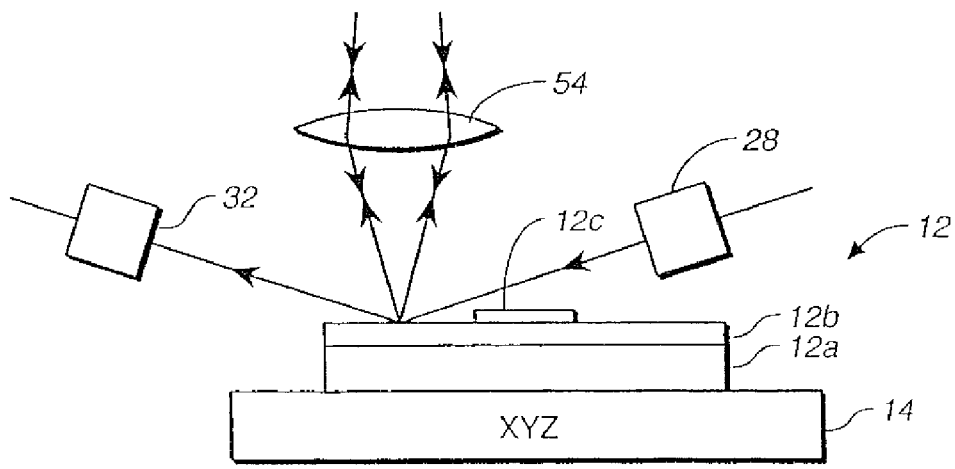
FIG._1B
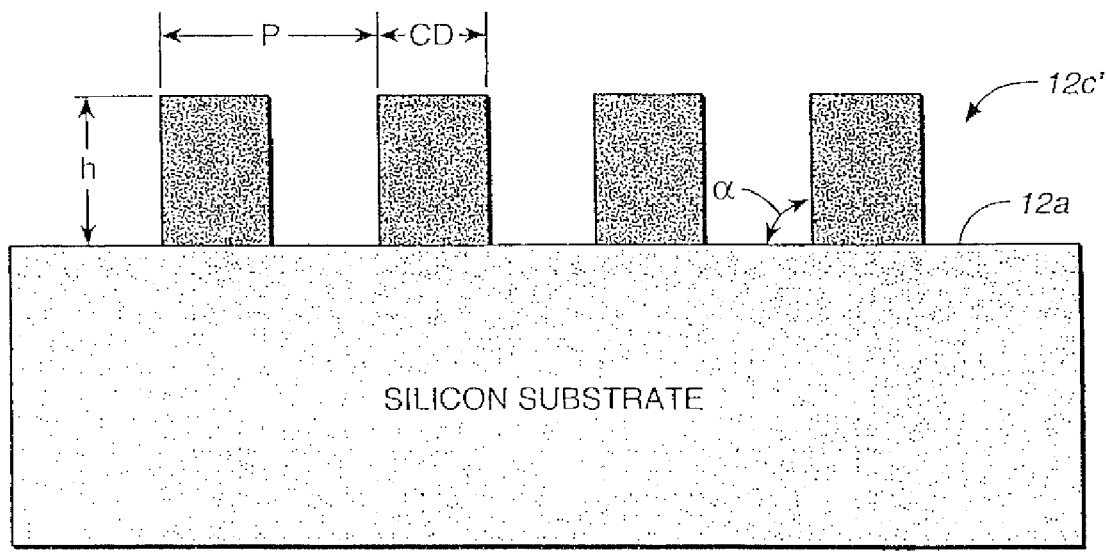
FIG._2

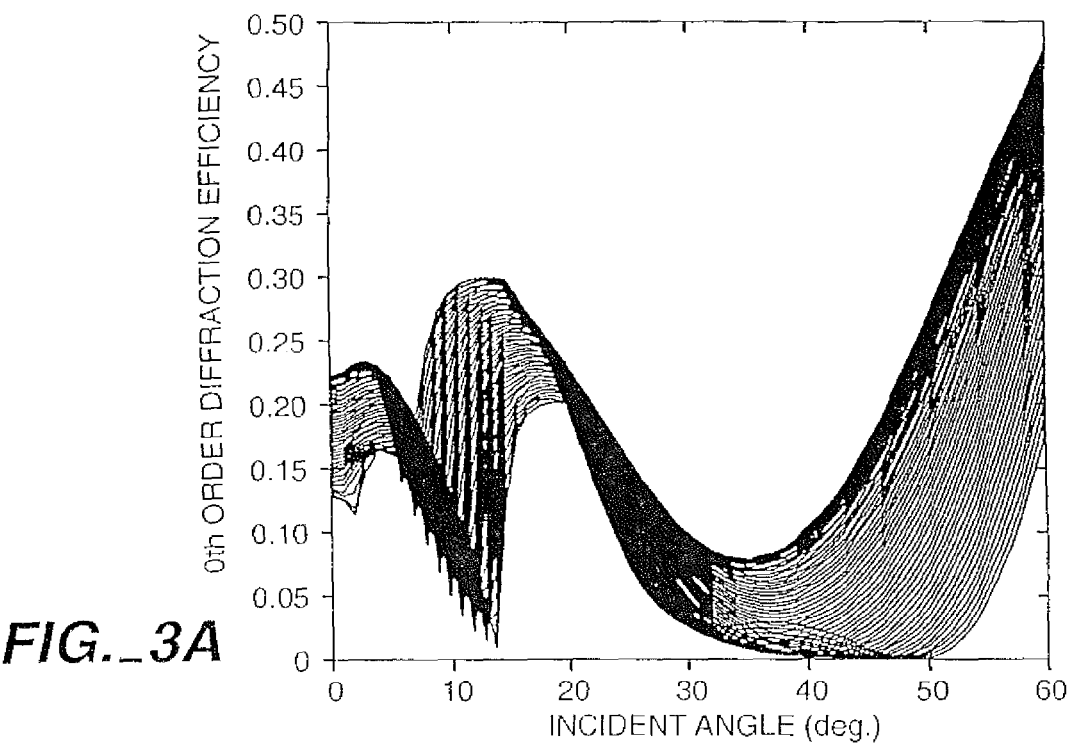
FIG._3A
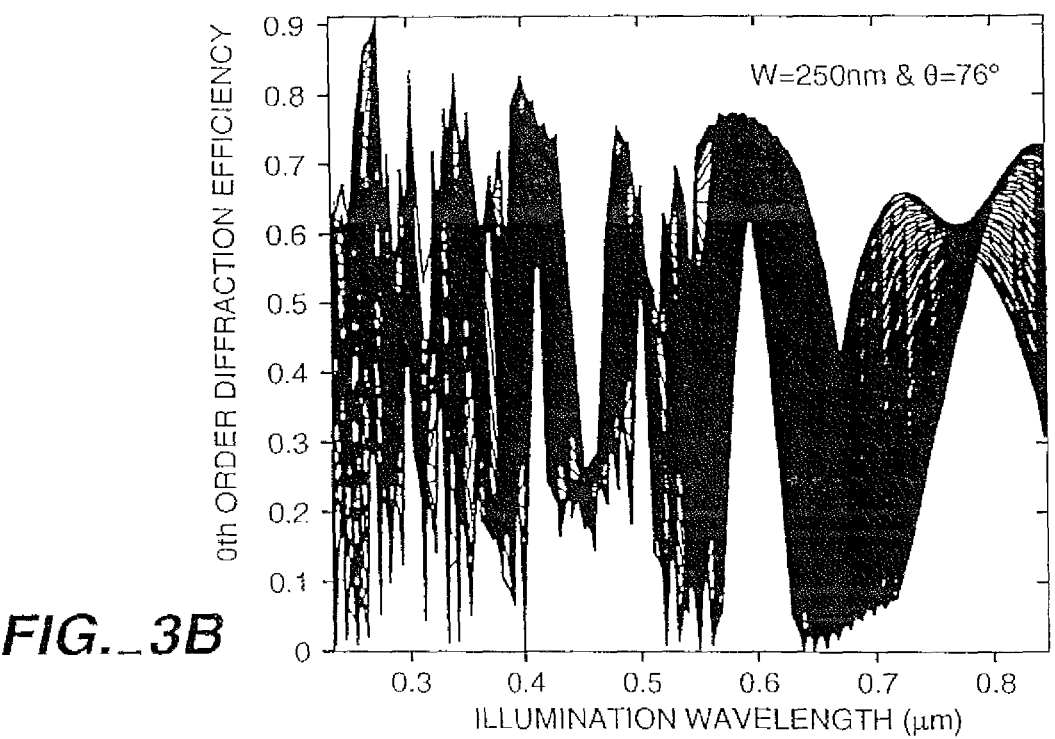
FIG._3B

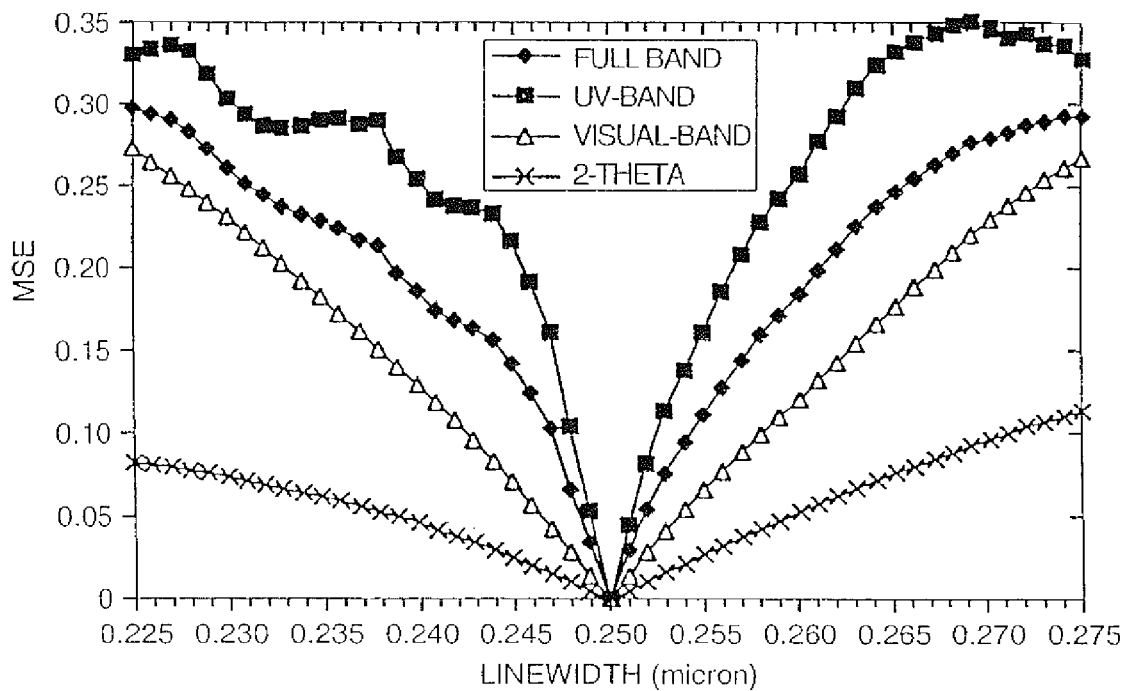
FIG._3C
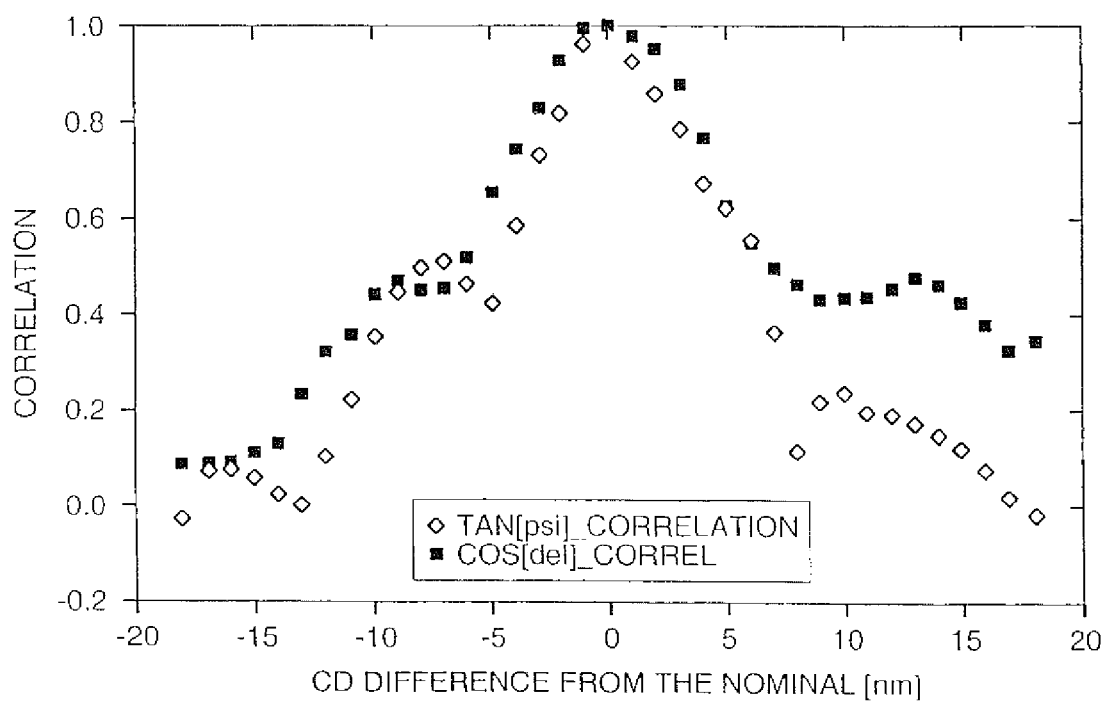
FIG._5

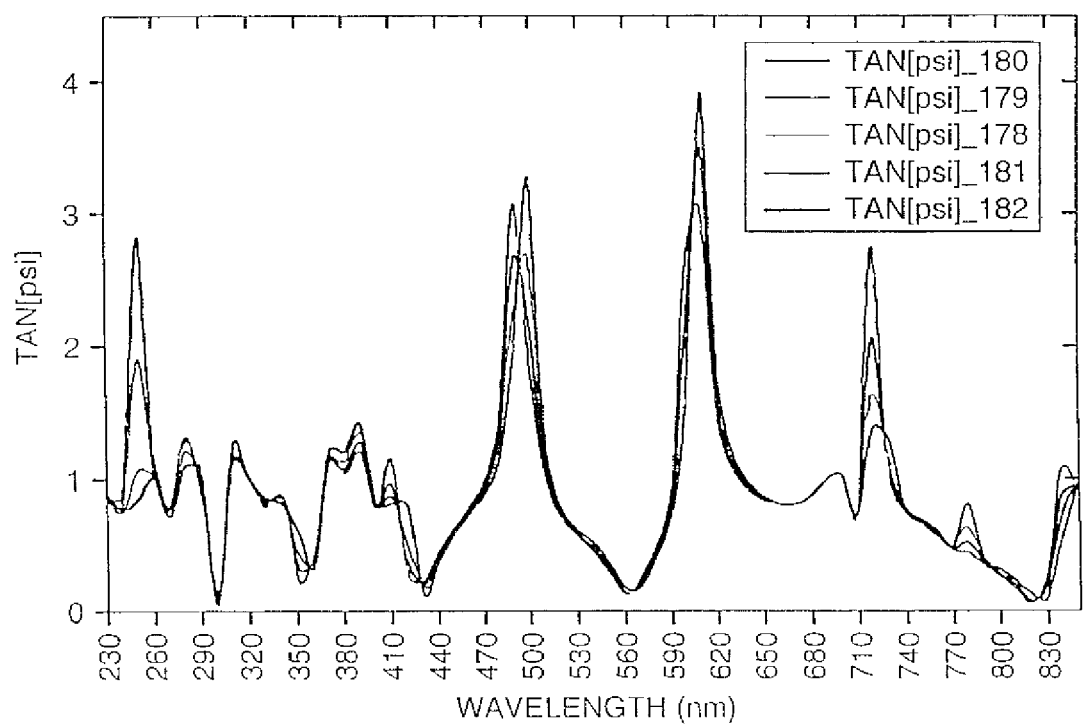
FIG._4A
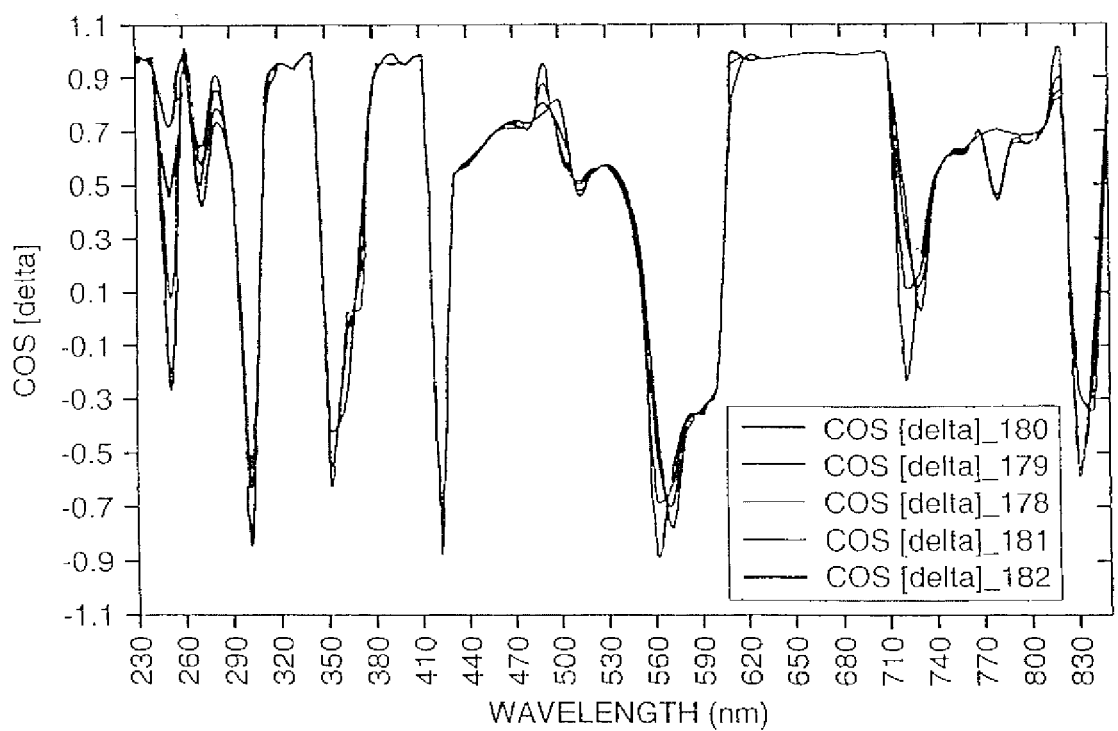
FIG._4B

SPECTROSCOPIC SCATTEROMETER SYSTEM

CROSS-REFERENCE TO RELATED APPLICATIONS

This application claims the benefit of U.S. Non-provisional application Ser. No. 11/614,315, entitled "SPECTROSCOPIC SCATTEROMETER SYSTEM" and filed on Dec. 21, 2006 which claims the benefit of U.S. Non-provisional application Ser. No. 10/251,246, entitled "SPECTROSCOPIC SCATTEROMETER SYSTEM" and filed on Sep. 20, 2002, which claims the benefit of U.S. Non-provisional application Ser. No. 09/036,557, entitled "SPECTROSCOPIC SCATTEROMETER SYSTEM" and filed on Mar. 6, 1998 and the aforementioned applications are incorporated herein in their entirety by this reference

BACKGROUND OF THE INVENTION

This invention relates in general to scatterometers and in particular, to a spectroscopic scatterometer system.

As the integration and speed of microelectronic devices increase, circuit structures continue to shrink in dimension size and to improve in terms of profile edge sharpness. The state-of-the-art devices require a considerable number of process steps. It is becoming increasingly important to have an accurate measurement of submicron linewidth and quantitative description of the profile of the etched structures on a pattern wafer at each process step. Furthermore, there is a growing need for wafer process monitoring and close-loop control such as focus-exposure control in photolithography.

Diffraction-based analysis techniques such as scatterometry are especially well suited for microelectronics metrology applications because they are nondestructive, sufficiently accurate, repeatable, rapid, simple and inexpensive relative to critical dimension-scanning electron microscopy (CD-SEM).

Scatterometry is the angle-resolved measurement and characterization of light scattered from a structure. For structures that are periodic, incident light is scattered or diffracted into different orders. The angular location $\theta_r$ of the $m^{th}$ diffraction order with respect to the angle of incidence $\theta_i$ is specified by the grating equation:

$$\sin\theta_1 + \theta_r = m\frac{\lambda}{d} \quad (1)$$

where $\lambda$ is the wavelength of incident light and d the period of the diffracting structure.

The diffracted light pattern from a structure can be used as a "fingerprint" or "signature" for identifying the dimensions of the structure itself. In addition to period, more specific dimensions, such as width, step height, and the shape of the line, the thickness of the underlay film layers, and angle of the side-walls, referred to below as parameters of the structure, can also be measured by analyzing the scatter pattern.

Since the periods of the gratings in the state-of-the-art devices are generally below 1µ only the $0^{th}$ and $+/-1^{ST}$ diffraction orders exist over a practical angular range. A traditional scatterometer that measures the entire diffraction envelope does not provide the data required for an accurate analysis. One prior optical technique for characterizing submicron periodic topographic structures is called 2-$\ominus$ scatterometry.

The 2-$\ominus$ scatterometer monitors the intensity of a single diffraction order as a function of the angle of incidence of the illuminating light beam. The intensity variation of the $0^{th}$ as well as higher diffraction orders from the sample provides information which is useful for determining the properties of the sample which is illuminated. Because the properties of a sample are determined by the process used to fabricate the sample, the information is also useful as an indirect monitor of the process.

In 2-$\ominus$ scatterometry, a single wavelength coherent light beam, for example, a helium-neon laser, is incident upon a sample mounted on a stage. By either rotating the sample stage or illumination beam, the angle of incidence on the sample is changed. The intensity of the particular diffraction order (such as zeroth-order or first order) as a function of incident angle, which is called a 2-$\ominus$ plot or scatter "signature" is then downloaded to a computer. In order to determine the different parameters such as linewidth, step height, shape of the line, and angle of the side-walls (the angle the side-wall makes with the underlying surface, also known as the "wall angle"), a diffraction model is employed. Different grating parameters outlined above are parameterized and a parameter space is defined by allowing each grating-shaped parameter to vary over a certain range.

A rigorous diffraction model is used to calculate the theoretical diffracted light fingerprint from each grating in the parameter space, and a statistical prediction algorithm is trained on this theoretical calibration data. Subsequently, this prediction algorithm is used to determine the parameters that correspond to the 2-$\ominus$ plots or scatter "signature" measured from a target structure on a sample.

While 2-$\ominus$ scatterometry has been useful in some circumstances, it has many disadvantages. The periodic diffracting structure is frequently situated over one or more films that transmit light. Therefore, any diffraction model employed must account for the thicknesses and refractive indices of all films underneath the diffracting structure. In one approach, the thickness and refractive indices of all layers must be known in advance. This is undesirable since frequently, these quantities are not known in advance. In particular, the film thickness and optical indices of materials used in semiconductor fabrication often vary from process to process.

Another approach to solve the above problem is to include all unknown parameters in the model, including film thickness and optical indices of underlying film materials. By thus increasing the number of variables in the model, the number of signatures that has to be calculated increase exponentially, so that the computation time involved renders such approach inappropriate for real-time measurements.

Furthermore, since the intensity of the particular diffraction order as a function of incidence angle of the sampling beam is acquired sequentially as the incident angle is varied, data acquisition for the 2-$\ominus$ plot or scatter "signature" is slow and the detected intensity is subject to various noise sources such as system vibration and random electronic noise which may change over time as the incident angle is varied.

Another approach is proposed by Ziger in U.S. Pat. No. 5,607,800. In this approach, where the measurement of a particular patterned film is desired, a first patterned arrangement having predetermined and known grating characteristics close to those of the patterned film to be measured is first made, such as by forming a line-and-space pattern on a first wafer. A spectroreflectometer is then used to measure the amplitude of reflected signals from such first arrangement to obtain a signature. Then a second patterned arrangement having known grating characteristics close to those of the patterned film to be measured, such as another line-and-space pattern on a second wafer, is obtained and a spectroreflectometer is used to measure the amplitude of reflected signal from such arrangement to obtain a second signature. The process is repeated on additional wafers and the signatures so formed are organized as a database. Then, the target pattern film of the sample is measured using a spectroreflectometer and its signature compared to those present in the database. The signature in the database that matches the signature of the target film is then used to find the grating characteristics or parameters of the target film.

Ziger's approach is limited and impractical, since it requires replication of multiple reference patterns analogous to the target pattern and measurements of such reference patterns to construct a database before a measurement can be made of the target pattern. Ziger's approach also requires contrast difference between the reflectivity of the film versus the reflectivity of the substrate. In other words, Ziger's method cannot be used to measure the grating characteristics on line patterns made of a material having a reflectivity similar to that of the underlying substrate.

None of the above-described approaches is entirely satisfactory. It is therefore desirable to provide an improved scatterometer with better performance.

SUMMARY OF THE INVENTION

One aspect of the invention is directed towards a method of measuring one or more parameters of a diffracting structure on an underlying structure, said underlying structure having a film thickness and an optical index, comprising providing an optical index and a film thickness of the underlying structure; constructing a reference database of one or more parameters related to said diffracting structure using said optical index and film thickness of the underlying structure; and directing a beam of electromagnetic radiation at a plurality of wavelengths at said diffracting structure. The method further comprises detecting intensities or ellipsometric parameters at said plurality of wavelengths of a diffraction from said structure; and comparing said detected intensities or ellipsometric parameters to said database to determine said one or more parameters.

Another aspect of the invention is directed towards an apparatus for measuring one or more parameters of a diffracting structure on an underlying structure, said underlying structure having a film thickness and an optical index, comprising means for constructing a reference database of one or more parameters related to said diffracting structure using an optical index and a film thickness of the underlying structure; and means for directing a beam of electromagnetic radiation including energy at a plurality of wavelengths at said diffracting structure. The apparatus further comprises means for detecting intensities or ellipsometric parameters of a diffraction from said structure at said plurality of wavelengths; and means for comparing said detected intensities or ellipsometric parameters to said database to determine said one or more parameters.

Another aspect of the invention is directed towards a scatterometer for measuring a parameter of a diffracting structure of a sample, including a source which emits broadband radiation; a polarizer that polarizes the broadband radiation to produce a sampling beam sampling the structure; and means for detecting intensities or ellipsometric parameters of a-diffraction from the structure over a range of wavelengths.

An additional aspect of the invention is directed towards a method for measuring one or more parameters of a diffracting structure of a sample, including providing broadband radiation; polarizing the broadband radiation to produce a sampling beam; and directing the sampling beam towards the structure. The method further comprises detecting radiation of the sampling beam that has been diffracted from the structure over a range of wavelengths; and comparing the detected radiation to a reference to determine said one or more parameters.

One more aspect of the invention is directed towards an instrument for measuring one or more parameters of a diffracting structure on an underlying structure of a sample, comprising a source of broadband radiation; a polarizer polarizing said radiation to provide a sampling beam towards the sample; and an analyzer for receiving diffracted radiation from the structure to provide an output beam. The instrument further comprises a spectrometer detecting the output beam.

One more aspect of the invention is directed towards a method for measuring one or more parameters of a diffracting structure on an underlying structure of a sample, comprising performing spectroscopic measurements on the underlying structure to determine its characteristics; constructing a reference database of one or more parameters related to said diffracting structure using characteristics of the underlying structure; and performing scatterometric measurements on the diffracting structure to obtain intensity or ellipsometric data; and comparing said intensity or ellipsometric data to the reference database to derive said one or more parameters.

Yet another aspect of the invention is directed towards an instrument for measuring a sample, comprising a spectroscopic device measuring film thickness data, and index of refraction data of the sample over a spectrum; a scatterometer measuring diffraction data from a diffracting structure of said sample over a spectrum and means for deriving physical parameters related to the structure from the film thickness data, index of refraction data, and diffraction data.

BRIEF DESCRIPTION OF THE DRAWINGS

FIG. 1A is a schematic view of a spectroscopic scatterometer to illustrate the preferred embodiment of the invention.

FIG. 1B is a schematic view of a portion of the spectroscopic scatterometer of FIG. 1A to illustrate the preferred embodiment of the invention.

FIG. 2 is a cross-sectional view of a semiconductor wafer including a line pattern of photoresist on a bare silicon substrate useful for illustrating the invention.

FIG. 3A is a graphical plot of the intensity of the zeroth diffraction order as 51 different functions of the angle of incidence of the illuminating light beam in a 2-$\Theta$ scatterometer, where the nominal linewidth is assumed to be 250 nanometers, and the 51 functions are obtained assuming linewidths from 225 to 275 nanometers, at 1 nanometer steps, for comparison with predicted results of the invention.

FIG. 3B is a graphical plot of the intensity of the zeroth diffraction order as 51 different functions of the wavelength of the illuminating light beam according to the invention where the nominal linewidth is assumed to be 250 nanometers, and the 51 functions are obtained assuming linewidths from 225 to 275 nanometers, at 1 nanometer steps, for comparison with predicted results of the invention.

FIG. 3C is a plot of the means square error difference measurement as a function of linewidth, between the signature generated for the grating having the nominal linewidth of 250 nanometers and other signatures obtained for other linewidths using 2-$\Theta$ scatterometry, and using the preferred embodiment of this invention over a full range of the spectrum and over UV and visual wavelength bands of the full spectrum useful for illustrating the invention.

FIG. 4A is a graphical plot of the intensity of an ellipsometric parameter tan (psi) as 5 different functions of the wavelength of the illuminating light beam according to the invention where the nominal linewidth is assumed to be 180 nanometers, and the 5 functions are obtained assuming linewidths at 178, 179, 180, 181, 182 nanometers, for comparison with predicted results of the invention.

FIG. 4B is a graphical plot of the intensity of an ellipsometric parameter cos (delta) as 5 different functions of the wavelength of the illuminating light beam according to the invention where the nominal linewidth is assumed to be 180 nanometers, and the 5 functions are obtained assuming linewidths at 178, 179, 180, 181, 182 nanometers, for comparison with predicted results of the invention.

FIG. 5 is a plot of two sets of correlation functions between the signature for the grating having the nominal linewidth of 180 nanometers and other signatures for gratings at other linewidths, one set obtained using tan (psi) and the other set obtained using cos (delta).

For simplicity in description, identical components are identified by the same numerals in this application.

DETAILED DESCRIPTION OF THE PREFERRED EMBODIMENT

This invention is based on the recognition that, by measuring or otherwise obtaining characteristics such as the film thickness and optical index of the underlying films underneath the diffracting structure, the subsequent tasks of construction of a database and matching a signature of the diffracting structure to the database are much simplified. Furthermore, if spectroscopic ellipsometry is used to measure the film thickness and optical index of the underlying film(s) under the diffracting structure, an instrument which can be used for spectroscopic ellipsometry as well as for spectroscopic scatterometry may be provided for carrying out both functions. In the preferred embodiment, the spectroscopic ellipsometer and its associated spectroscopic scatterometer in the instrument may share many common optical elements to reduce the cost of the combined instrument and simplify its operation.

By first measuring the film thickness and optical refractive index of the underlying films, one no longer needs to include such parameters in the computation of the model or database and subsequent matching of signatures that much simplifies the computation task.

FIG. 1A is a schematic view of a spectroscopic scatterometer system to illustrate the preferred embodiment of the invention. As shown in FIG. 1A, system 10 advantageously combines features of a spectroscopic scatterometer, spectroscopic ellipsometer and spectroscopic reflectometer. The spectroscopic reflectometer or the spectroscopic ellipsometer may be used for measuring the film thickness and refractive index of the underlying structure underneath the diffracting structure. As shown in FIG. 1A, a semiconductor wafer may comprise a silicon substrate 12a, a film 12b on the substrate and a diffracting structure 12c such as a photoresist pattern on the film, where the film is at least partially light-transmissive and has a certain film thickness and refractive index (n and k, the real and imaginary components of the index).

Before the diffracting structure 12c is measured, an XYZ stage 14 is used for moving the wafer in the horizontal XY directions in order to first measure the film thickness and refractive index of the underlying structure underneath the photoresist pattern 12c. Stage 14 may also be used to adjust the z height of the wafer 12 as described below. Stage 14 moves the wafer to a position as shown in FIG. 1B so that the sampling beam of radiation illuminates a portion of film 12b away from structure 12c. In reference to FIGS. 1A, 1B, for the purpose of measuring the film thickness and refractive index of the underlying structure (12b and 12a), a broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 230 to 800 nm. Upon emerging from fiber 24, the radiation passes through an optical illuminator that may include a slit aperture and a focus lens (not shown). The slit aperture causes the emerging light beam to image a small area of layer 12b. The light emerging from illuminator 26 is polarized by a polarizer 28 to produce a polarized sampling beam 30 illuminating the layer 12b.

The radiation originating from sampling beam 30 that is reflected by layer 12b, passed through an analyzer 32 and to a spectrometer 34 to detect different spectral components of the reflected radiation. In the spectroscopic ellipsometry mode of system 10 for measuring film thickness and refractive index, either the polarizer 28 or the analyzer 30 is rotated (to cause relative rotational motion between the polarizer and the analyzer) when spectrometer 34 is detecting the reflected light at a plurality of wavelengths, such as those in the spectrum of the radiation source 22, where the rotation is controlled by computer 40 in a manner known to those skilled in the art. The reflected intensities at different wavelengths detected is supplied to computer 40 which computes the film thickness and n and k values of the refractive index of layer 12b in a manner known to those skilled in the art. For a description of a spectroscopic ellipsometer, please see U.S. Pat. No. 5,608,526, issued Mar. 4, 1997.

While spectroscopic ellipsometry may be preferred for measuring film thickness and refractive index, in some applications where there may only be one or two relatively thick films underneath the diffracting structure, a spectroscopic reflectometer (also known as spectroreflectometer and spectrophotometer) may be adequate for measuring the film thickness and refractive index. For this purpose, lens 23 collects and directs radiation from source 22 to a beam splitter 52, which reflects part of the incoming beam towards the focus lens 54 which focuses the radiation to layer 12b. The light reflected by the layer 12b is collected by lens 54, passes through the beam splitter 52 to a spectrometer in the spectroscopic reflectometer 60. The spectral components at different wavelengths measured are detected and signals representing such components are supplied to computer 40 for determining the film thickness and refractive index in a manner described, for example, in U.S. patent application Ser. No. 08/227,482, filed Apr. 14, 1994. Spectroscopic devices other than the spectroscopic reflectometer and spectroscopic ellipsometer may also be used for measuring the film thickness and refractive index of layer 12b and are within the scope of the invention. An example of such spectroscopic devices include the n & k Analyzer of n & k Technology Inc. of Santa Clara, Calif., and described in "Optical Characterization of Amorphous and Polycrystalline Silicon Films," by Ibok et al., reprinted from August 1995 edition of *Solid State Technology* published by PennWell Publishing Company; "Optical Dispersion Relations for Amorphous Semiconductors and Amorphous Dielectrics," by Forouhi et al., *Physical Review B*, vol. 34, no. 10, pp 7018-7026, Nov. 15, 1986; "Optical Properties of Crystalline Semiconductors and Dielectrics," by Forouhi et al., *Physical Review B*, vol. 38, no. 3, pp 1865-1874, Jul. 15, 1988 and U.S. Pat. No. 4,905,170.

For the purpose of adjusting the height of wafer 12 relative to the polarizer 28, analyzer 32 to achieve proper focus in the spectroscopic ellipsometry measurement, or relative to the focus lens 54 and spectroscopic reflectometer 60 in the spectroreflectometer measurement, the height of the wafer may need to be adjusted by means of stage 14 prior to the measurement. For this purpose, a portion of the radiation reflected by layer 12b (or layer 12c in the, description that follows) and collected by lens 54 is reflected by a beamsplitter 62 towards a focusing and pattern recognition block 64 for comparing the reflected image to a pattern. Block 62 then sends information concerning the comparison to computer 40 which controls stage 14. Stage 14, in turn, moves the wafer 12 up or down in the vertical or Z direction in order to move wafer 12 to a proper height relative to the optical components of system 10.

Once the film thickness and refractive index of the one or more films underneath the diffracting structure 12c have been so measured, a reference database may now be constructed by means of computer 40. Where the film thickness and refractive index of the one or more films underneath the diffracting structure 12c are known to begin with, or can be estimated, it is possible to omit the step of measuring these quantities. To construct the reference database, characteristics concerning the diffracting structure 12c may be parameterized and the parameters database is defined by allowing an unknown grating parameter of the structure, such as linewidth, height and wall angle to vary over a certain range. This is illustrated by reference to FIG. 2.

FIG. 2 is a cross-sectional view of a semiconductor wafer comprising a silicon substrate 12a and a diffracting structure 12c' having a linewidth CD, pitch p, height h, and wall angle a as shown in FIG. 2. Thus, the grating shape parameters that can be parameterized and varied over a certain range include CD, h and a. A rigorous diffraction model, such as the model method by modal expansion (MMME), is used to calculate the theoretical diffracted light fingerprint from each grating in the parameter space, and a, statistical prediction algorithm such as Partial-Leased-Squares (PLS) or Minimum-Mean-Square-Error (MMSE) is trained on this theoretical calibration data. For a description of the MMME, please see "Convergence of the Coupled-wave Method for Metallic Lamellar Diffraction Gratings," by Li et al., *Journal of the Optical Society of America A* Vol. 10, No. 6, pp. 1184-1189, June 1993; and "Multilayer Modal Method for Diffraction Gratings of Arbitrary Profile, Depth, and Permittivity," by Li et al., *Journal of the Optical Society of America A* Vol. 10, No. 12, pp. 2582-2591, December 1993.

Instead of using the MMME, the grating shape parameters can also be parameterized using rigorous coupling waveguide analysis ("RCWA"). Such method is described, for example, in "Rigorous coupled-wave analysis of planar-grating diffraction," by M. Moharam et al., *J. Opt. Soc. Am.*, Vol. 71, No. 7, July 1981, pp. 811-818, "Stable implementation of the rigorous coupled-wave analysis for surface-relief gratings: enhanced transmittance matrix approach," by M. Moharam et al., *J. Opt. Soc. Am.* A, Vol. 12, No 5, May 1995, pp. 1077-1086, and "Analysis and Applications of Optical Diffraction by Gratings," T. Gaylord et al., *Proceedings of the IEEE*, Vol. 73, No. 5, May 1985, pp. 894-937.

Where more than one grating shape parameter is varied, the calculation of fingerprints may be performed by varying only one parameter at a time while keeping the other parameters at selected constant values within selected ranges. Then another parameter is allowed to vary and so on. Subsequently, this prediction algorithm is used to determine the values of the parameters that correspond to the fingerprint measured from layer 12c'.

Since the film thickness and optical indices of any film underlying diffracting structure 12c or 12c' are known from the spectroscopic ellipsometry or spectroreflectometry measurements, or are otherwise known, these values may be used in construction of the reference database so that the film thickness and refractive index need not be parameters in the database. This greatly reduces the number of variables in the parameter space and also greatly reduces the number of signatures that need to be calculated for the reference database. Thus, compared to the 2-Θ scatterometry method where such variables need to be taken into account in the parameter space and the calculation of signatures, this invention enables a smaller database to be used when searching for solutions. Furthermore, due to the number of variables that are parameterized in such 2-Θ scatterometry method, there may be multiple solutions which causes difficulties in obtaining a correct solution. By reducing the size of the database, this invention enables unique solutions to be found in most cases. In this manner, this invention reduces the computation time by many orders of magnitude compared to 2-Θ scatterometry.

The process for measuring the signature from layer 12c and 12c' will now be described in reference to FIG. 1A. As described above, stage 14 moves wafer 12 so that the sampling beam 30 illuminates an area of the underlying film 12b without illuminating any portion of the diffracting structure 12c. Now in order to measure structure 12c, the computer 40 causes stage 14 to move the wafer along a direction in the XY plane so that the sampling beam 30 impinges on layer 12c (or 12c' in FIG. 2). Broadband radiation from source 22 is polarized by polarizer 28 into a polarized broadbeam sampling beam 30. A diffraction of beam 30 is supplied to spectrometer 34 which measures substantially simultaneously the radiation intensities at different wavelengths of a diffraction from structure 12c, such as at wavelengths across the spectrum of radiation source 22. In the preferred embodiment, the zeroth diffraction order intensity is measured, although for some structures, measurement of higher diffraction order intensities may also be feasible. The process just described is the scatterometric measurement mode of system 10.

Zeroth or higher diffraction order intensities at different wavelengths detected by spectrometer 34 are supplied to computer 40 for analysis and determination of a signature of structure 12c or 12c'. This signature is then compared to those precomputed in the reference database in the manner described above. The grating shape parameters of the signature in the reference database that matches the measured signature of structure 12c or 12c' are then the grating shape parameters of the structure.

In the scatterometric measurement mode, analyzer 32 may be simply removed from the optical path from structure 12c to spectrometer 34. Alternatively, polarizer 28 and analyzer 32 may be controlled by means of computer 40 so that polarizer 28 passes radiation of a certain polarization and analyzer 32 is oriented to pass radiation of the same polarization as that passed by polarizer 28. This invention is based on the discovery that, where the incidence plane of the beam 30 is substantially normal to the grating 12c, the sensitivity of scatterometric measurements is improved if polarizer 28 is oriented to supply a sampling beam 30 polarized in the TE mode (S-polarized) and analyzer 32 is oriented to pass light in the TE mode. Alternatively, where the incidence plane of the beam 30 is substantially parallel to the grating 12c, the sensitivity of scatterometric measurements is improved if polarizer 28 is oriented to supply a sampling beam 30 polarized in the TM mode (P-polarized) and analyzer 32 is oriented to pass light in the TM mode.

If more than one diffracting structure having different shape parameters are present on wafer 12, stage 14 may be controlled by computer 40 to move wafer 12 so that the sampling beam 30 is directed towards each of such diffracting structures one at a time. System 10 is then operated in the scatterometric measuring mode to obtain signatures from each of such diffracting structures. The signature of each diffracting structure may then be matched with a signature in the reference database in order to obtain the grating shape parameters of such structure. It will be noted that, where measurement of the characteristics of the underlying structure (12a, 12b) is necessary, this will need to be performed only once for each wafer and the reference database will need to be constructed only once for the wafer as well. After these have been accomplished, the scatterometric measurements of the different diffracting structures on wafer 12 may be performed quickly and the signatures of each diffracting structure matched to the reference database expeditiously. As noted above, since the reference database contains a smaller number of signatures, the matching or prediction speed of the grating shape parameters of the different diffracting structures on wafer 12 is greatly increased. This makes real time and in-line measurements of the diffracting structures possible. In some applications, a number of semiconductor wafers made by the same process have the same underlying structure underneath the diffraction structures; these underlying structures of the different wafers may have substantially the same film thicknesses and indices of refraction. If this is the case, the above-described process for measuring film thickness and index refraction and the construction of the reference database may need to be performed only once for the entire batch of wafers made by the same process, if the tolerance of the process is known. This further speeds up the measurement and calculation process.

As compared to 2-$\Theta$ scatterometry, the spectroscopic scatterometer of this invention measures diffraction and a number of wavelengths simultaneously. This is in contrast to 2-$\Theta$ scatterometry where the user takes a measurement of the diffraction at one angle of incidence at a time. Such feature also speeds up the measurement process. It will also be noted that the above-described reference database is constructed without the use of reference samples. Thus, the user does not have to make reference wafers having diffracting structures analogous to the one being measured or having to take measurements from such reference samples before a database can be constructed. Furthermore, a rigorously radical model such as MMME is used to achieve accurate results.

Preferably, in the spectroscopic ellipsometry mode and the scatterometric measurement mode, sampling beam 30 is directed towards wafer 12 at an oblique angle to layer 12b and 12c. Sampling beam 30 is preferably at an oblique angle in the range of 40 to 80°, and more preferably in the range of 60 to 80° for measurement of silicon wafers, from a normal to the layers on the wafer 12. A particularly preferred angle of incidence from the normal is about 76° which is substantially the Brewster angle for silicon. In system 10, the spectroscopic ellipsometer and spectroscopic scatterometer advantageously employ many common optical elements, such as the broadband source 22, fiber 24, illuminator 26, polarizer 28 and spectrometer 34. This simplifies the design of system 10, reduces cost and simplifies its operation.

The process for adjusting the height of wafer 12 relative to the optical components in the spectroreflectometry and spectroscopic ellipsometry modes has been described above. However, when light reflected from beamsplitter 52 is directed towards a diffracting structure such as 12c, it is preferable for the light so reflected to be polarized and to have the same polarization as that in sampling beam 30 when the height of the wafer 12 is adjusted. For this purpose, radiation supplied by source 22 is passed through a polarizer 72 before it is directed to beamsplitter 52. The optical axis of polarizer 72 is controlled by computer 40 so that it has the same orientation as the optical axis of polarizer 28 when the focusing and pattern recognition block 64 is used to detect radiation reflected from structure 12c and stage 14 is controlled by computer 40 to adjust height of the wafer until it is at the proper height relative to the sampling beam 30. Polarizer 72 does not affect the height adjustment process during the spectroreflectometry and spectroscopic ellipsometry modes or the spectroscopic reflectometry measurements. The polarized radiation detected by spectroscopic reflectometer 60 may also be used to normalize the intensity measurement in the scatterometer mode described above at an oblique angle to reduce the effects of intensity variations of source 22.

FIG. 3A is a graphical plot of the intensity of the zeroth diffraction order as 51 functions of the angle of incidence of the illuminating light beam in a 2-$\Theta$ scatterometer measuring structure 12c' of FIG. 2, where the nominal linewidth is assumed to be 250 nm, and the 51 functions are obtained assuming linewidths from 225 to 275 nanometers, at 1 nanometer steps. The incidence angles used in a calculation of the graphical plot in FIG. 3A varies from 0 to 60° with an uniform increment of 1°, which results in 61 datapoints per signature curve. The light beam is assumed to be TE polarized and the wavelength was 0.6328 microns.

FIG. 3B is a graphical plot of the intensity of zeroth diffraction order as a function of the wavelength of the illuminating light beam according to the invention used for measuring structure 12c' of FIG. 2 where the nominal linewidth is assumed to be 250 nm, and the 51 functions are obtained assuming linewidths from 225 to 275 nanometers, at 1 nanometer steps. These 51 functions are obtained by means of the MMME model method rigorous diffraction method described above, making use of the known or measured index of refraction and film thickness information. These curves are used in comparison with measured results of the invention to predict linewidth of the measured structure. The intensity of the zeroth order is calculated as a function of the wavelength of the illuminating light beam and the wavelengths used in the calculation varies from 0.23 to 0.850 microns with an uniform increment of 0.01 micron which results in 63 datapoints per signature curve. The light beam is assumed to be TE polarized and is illuminated at an oblique angle of 76° from the normal.

FIG. 3C is a plot of the mean squares error difference measurement as a function of linewidth, between the signature generated for the grating having the linewidth of 250 nm and other signatures obtained at other linewidths using 2-$\Theta$ scatterometry. FIG. 3C also shows plots of the mean squares error difference measurement as a function of linewidth, between the signature generated for the grating having the linewidth of 250 nm and other signatures obtained at other linewidths, and using the preferred embodiment of this invention over a full range of the spectrum as well as over ultraviolet (UV) and visual wavelength bands of the full spectrum. As will be evident from FIG. 3C, the spectroscopic scatterometer of this invention is more sensitive than the 2-$\Theta$ scatterometer. The mean square area difference for 1 nm linewidth (CD) sensitivity are shown by Tables 1 and 2 below.

TABLE 1

| MSE Different for 1 nm CD Sensitivity | | | | |
|---|---|---|---|---|
| CD (nm) | Full Band | UV Band | Visual Band | 2-$\Theta$ |
| 250 | 0.0339 | 0.0528 | 0.0142 | 0.0051 |

TABLE 2

| | MSE Ratio With Respect to 2-Θ | | |
|---|---|---|---|
| CD (nm) | Full Band | UV Band | Visual Band |
| 250 | 6.62 | 10.31 | 2.78 |

From FIG. 3C, it is also evident that the sensitivity may be higher if only data collected using radiation at a sub-band of the full spectrum is used for matching the signature. Thus, even though the spectrometer 34 records the diffraction for the full range of wavelengths in the spectrum, sensitivity may be improved if only the diffraction at wavelengths in the ultraviolet (UV) band is used to construct the measured signatures from the diffracting structure of 12c and 12c'. Such signatures are then matched to signatures in the database calculated for the UV band as well. From FIG. 3B, it is noted that each of the curves is a function characterizing a particular signature of a grating. While in FIG. 3C, information in the ultraviolet band may provide higher sensitivity compared to the visual band or the full band, information in a different portion of the spectrum may provide better sensitivity for gratings of other shapes and dimensions. All such variations are within the scope of the invention.

Another aspect of the invention is based on the observation that, instead of detecting the intensity of the zero, first or other order of diffraction from structure 12c or 12c', the apparatus 10 of FIG. 1A may be used to detect ellipsometric parameters of such order diffraction from the structure for determining one or more parameters of the diffracting structure. In other words, during the scatterometer mode, computer 40 controls polarizer 28 and analyzer 32 to cause relative rotation and motion between them, and system 10 is used for measuring ellipsometric parameters such as tan (psi) and cos (delta) adds a plurality of wavelengths, such as at wavelengths in the spectrum of radiation source 22. With either known or measured index or refraction and film thickness information of the one or more underlying films underneath the structure 12c or 12c', the MMME model method described above may be used to construct a database of tan (psi) and cos (delta) as functions of wavelength, as illustrated in FIGS. 4A and 4B, corresponding to different values of parameters of the structure 12c or 12c'. Thus as shown in FIG. 4A, the model may be used to construct five functions for tan (psi) as functions of wavelength at five different linewidths. FIG. 4B illustrates a similar plot for the ellipsometric parameter cos (delta). The nominal linewidth is 180 nanometers. By measuring the two ellipsometric parameters of structure 12c or 12c' by means of system 10, the measured functions may be compared to those in FIGS. 4A and 4B to find the best fit. The sensitivity in using the ellipsometric parameters is illustrated in FIGS. 5. FIG. FIG. 5 is a plot of the correlation between the ellipsometric parameters corresponding to the nominal 180 nanometer value and those corresponding to the remaining four line width values. Other than the above noted differences, in this aspect of the invention where ellipsometric parameters are used for determining characteristics of the structure 12c, 12c', the system 10 operates in a manner and shares the same advantages essentially as those described above for measuring intensity of diffraction in determining characteristics of the structure 12c, 12c'. For some applications, measuring the ellipsometric parameters may offer higher sensitivity.

While the construction of database is illustrated above by reference to functions corresponding to different linewidths, it will be understood that similar functions may be constructed using the model for other parameters of the structure 12c or 12c', such as height or wall angle of the structure. Such and other variations are within the scope of the invention.

While the invention has been described by reference to various embodiments, it will be understood that different changes and modifications may be made without departing from the scope of the invention which is to be defined only by the appended claims and their equivalents.

What is claimed is:

1. A scatterometer for measuring one or more parameters of a periodic diffracting structure of a sample, said one or more parameters comprising shape of lines, linewidth, pitch, height and/or side wall angle of the periodic diffracting structure, said scatterometer comprising:
   a reference database that includes a plurality of ellipsometric functions, each ellipsometric function corresponding to a set of values of said one or more parameters, said values including at least values of line width, height and side wall angle of periodic diffracting structures;
   a source which emits broadband radiation;
   a polarizer that polarizes the broadband radiation to produce a sampling beam sampling the periodic diffracting structure;
   a detector detecting ellipsometric parameters of a diffraction from the periodic diffracting structure of said broadband radiation over a range of wavelengths;
   a processor comparing said detected ellipsometric parameters to said plurality of ellipsometric functions in said database to determine said shape of lines, linewidth, pitch, height and/or side wall angle of the periodic diffracting structure, wherein said processor determines at least the line width, height and side wall angle of the periodic diffracting structure; and
   a device measuring data related to at least an index of refraction of a structure adjacent to the periodic diffracting structure;
   said periodic diffracting structure located on a surface of a sample, wherein said adjacent structure is away from said periodic diffracting structure so that said data related to at least said index of refraction of the adjacent structure is measured without measuring said periodic diffracting structure, and the processor uses said data related to at least the index of refraction of the adjacent structure to reduce number of parameters of the database and processing time for determining said parameters of the periodic diffracting structure.

2. An instrument for measuring one or more parameters of a periodic diffracting structure located adjacent to a structure of a sample, said one or more parameters comprising shape of lines, linewidth, pitch, height and/or side wall angle of the periodic diffracting structure, said instrument comprising:
   a reference database that includes a plurality of ellipsometric functions, each ellipsometric function corresponding to a set of values of said one or more parameters, said values including at least values of line width, height and side wall angle of periodic diffracting structures;
   a source of broadband radiation;
   a polarizer polarizing said radiation to provide a sampling beam towards the sample;
   an analyzer for receiving radiation from the sampling beam diffracted by the periodic diffracting structure to provide an output beam;
   a spectrometer for detecting intensity data from the output beam simultaneously at a plurality of wavelengths;
   a device measuring data related to at least an index of refraction of the adjacent structure;
   a processor for controlling said polarizer and analyzer so that ellipsometric functions are measured, and determining at least the line width, height and side wall angle of the periodic diffracting structure by comparison of said measured ellipsometric functions to said ellipsometric functions in the reference database, said periodic diffracting structure located on a surface of a sample, wherein said adjacent structure is away from said periodic diffracting structure so that said data related to at least the index of refraction of the adjacent structure is measured without measuring said periodic diffracting structure, and the processor uses said data related to at least the index of refraction of the adjacent structure to reduce number of parameters of the database and processing time for determining said parameters of the periodic diffracting structure.

3. The instrument of claim 2, wherein said device comprises a spectroscopic ellipsometer, spectrophotometer or spectroreflectometer.

4. The instrument of claim 2, wherein said device also measures thickness of the adjacent structure.

5. A scatterometer for measuring one or more parameters of a periodic diffracting structure of a sample, said one or more parameters comprising shape of lines, linewidth, pitch, height and/or side wall angle of the periodic diffracting structure, said scatterometer comprising:
 a reference database that includes a plurality of ellipsometric functions, each ellipsometric function corresponding to a set of values of said one or more parameters, said values including at least values of line width, height and side wall angle of periodic diffracting structures;
 a source which emits broadband radiation;
 a polarizer that polarizes the broadband radiation to produce a sampling beam sampling the periodic diffracting structure;
 means for detecting ellipsometric parameters of a diffraction from the periodic diffracting structure of said broadband radiation over a range of wavelengths;
 means for comparing said detected ellipsometric parameters to said plurality of ellipsometric functions in the database to determine said shape of lines, linewidth, pitch, height and/or side wall angle of the periodic diffracting structure, wherein said comparing means determines at least the line width, height and side wall angle of the periodic diffracting structure; and
 a device measuring data related to at least an index of refraction of a structure adjacent to the periodic diffracting structure.

6. The scatterometer of claim 5, wherein said adjacent structure is away from said periodic diffracting structure so that said data related to at least the index of refraction of the adjacent structure is measured without measuring said periodic diffracting structure, and the comparing means uses said data related to at least the index of refraction of the adjacent structure to reduce number of parameters of the database and processing time for determining said parameters of the periodic diffracting structure.

7. The scatterometer of claim 5, wherein said device comprises a spectroscopic ellipsometer, spectrophotometer or spectroreflectometer.

8. The scatterometer of claim 5, wherein said device also measures a thickness of the adjacent structure.

9. The scatterometer of claim 8, wherein the thickness of the adjacent structure is not a parameter in the reference database.

10. The scatterometer of claim 5, wherein the index of refraction of the adjacent structure is not a parameter in the reference database.

11. A scatterometer for measuring one or more parameters of a periodic diffracting structure of a sample, said one or more parameters comprising shape of lines, linewidth, pitch, height and/or side wall angle of the structure, said scatterometer comprising:
 a reference database that includes a plurality of signature curves, each signature curve corresponding to a set of values of said one or more parameters, said values including at least values of line width, height and side wall angle of periodic diffracting structures;
 a source which emits broadband radiation;
 a polarizer that polarizes the broadband radiation to produce a sampling beam at an oblique angle to the sample sampling the periodic diffracting structure;
 a detector detecting intensity data of a diffraction from the periodic diffracting structure of said broadband radiation over a range of wavelengths; and
 a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure;
 said reference database constructed using information related to film thickness of an adjacent structure that is obtained without measuring said periodic diffracting structure.

12. A scatterometer for measuring one or more parameters of a periodic diffracting structure of a sample, said one or more parameters comprising shape of lines, linewidth, pitch, height and/or side wall angle of the structure, said scatterometer comprising:
 a reference database that includes a plurality of signature curves, each signature curve corresponding to a set of values of said one or more parameters, said values including at least values of line width, height and side wall angle of periodic diffracting structures;
 a source which emits broadband radiation;
 a polarizer that polarizes the broadband radiation to produce a sampling beam at an oblique angle to the sample sampling the periodic diffracting structure;
 a detector detecting intensity data of a diffraction from the periodic diffracting structure of said broadband radiation over a range of wavelengths; and
 a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure;
 said reference database constructed using an index of refraction of an adjacent structure that is obtained without measuring said periodic diffracting structure to reduce the number of signature curves in the reference database.

13. A scatterometer for measuring one or more parameters of a periodic diffracting structure of a sample, said one or more parameters comprising shape of lines, linewidth, pitch, height and/or side wall angle of the structure, said scatterometer comprising:
 a reference database that includes a plurality of signature curves, each signature curve corresponding to a set of values of said one or more parameters, said values including at least values of line width, height and side wall angle of periodic diffracting structures;

a source which emits broadband radiation;

a polarizer that polarizes the broadband radiation to produce a sampling beam at an oblique angle to the sample sampling the periodic diffracting structure;

a detector detecting intensity data of a diffraction from the periodic diffracting structure of said broadband radiation over a range of wavelengths; and a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure;

said sample comprising an adjacent structure having at least an index of refraction, said scatterometer further comprising a device measuring data related to said at least the index of refraction of the adjacent structure without measuring said periodic diffracting structure.

14. The scatterometer of claim 13, wherein the processor uses said data related to at least the index of refraction of the adjacent structure to reduce number of parameters of the database and processing time for determining said one or more parameters of the periodic diffracting structure.

15. A scatterometer for measuring one or more parameters of a periodic diffracting structure of a sample, said one or more parameters comprising shape of lines, linewidth, pitch, height and/or side wall angle of the periodic diffracting structure, said scatterometer comprising:

a reference database that includes a plurality of ellipsometric functions, each ellipsometric function corresponding to a set of values of said one or more parameters, said values including at least values of line width, height and side wall angle of periodic diffracting structures;

a source which emits broadband radiation;

a polarizer that polarizes the broadband radiation to produce a sampling beam sampling the periodic diffracting structure;

a detector detecting ellipsometric parameters of a diffraction from the periodic diffracting structure of said broadband radiation over a range of wavelengths;

a processor comparing said detected ellipsometric parameters to said plurality of ellipsometric functions in said database to determine said shape of lines, linewidth, pitch, height and/or side wall angle of the periodic diffracting structure, wherein said processor determines at least the line width, height and side wall angle of the periodic diffracting structure; and a device measuring data related to at least an index of refraction of a structure adjacent to and associated with the periodic diffracting structure, said periodic diffracting structure located on a surface of a sample, wherein said associated structure is away from said periodic diffracting structure so that said data related to at least said index of refraction of the associated structure is measured without measuring said periodic diffracting structure, and the processor uses said data related to at least the index of refraction of the associated structure to reduce number of parameters of the database and processing time for determining said parameters of the periodic diffracting structure.

16. An instrument for measuring one or more parameters of a periodic diffracting structure located adjacent to an associated structure of a sample, said one or more parameters comprising shape of lines, linewidth, pitch, height and/or side wall angle of the periodic diffracting structure, said instrument comprising:

a reference database that includes a plurality of ellipsometric functions, each ellipsometric function corresponding to a set of values of said one or more parameters, said values including at least values of line width, height and side wall angle of periodic diffracting structures;

a source of broadband radiation;

a polarizer polarizing said radiation to provide a sampling beam towards the sample;

an analyzer for receiving radiation from the sampling beam diffracted by the periodic diffracting structure to provide an output beam;

a spectrometer for detecting intensity data from the output beam simultaneously at a plurality of wavelengths;

a processor for controlling said polarizer and analyzer so that ellipsometric functions are measured, and determining at least the line width, height and side wall angle of the periodic diffracting structure by comparison of said measured ellipsometric functions to said ellipsometric functions in the reference database; and a device measuring data related to at least an index of refraction of the associated structure.

17. The instrument of claim 16, said periodic diffracting structure located on a surface of a sample, wherein said associated structure is away from said periodic diffracting structure so that said data related to at least the index of refraction of the associated structure is measured without measuring said periodic diffracting structure, and the processor uses said data related to at least the index of refraction of the associated structure to reduce number of parameters of the database and processing time for determining said parameters of the periodic diffracting structure.

18. The instrument of claim 16, wherein said device comprises a spectroscopic ellipsometer, spectrophotometer or spectroreflectometer.

19. The instrument of claim 16, wherein said device also measures thickness information of the associated structure.

20. A scatterometer for measuring one or more parameters of a periodic diffracting structure of a sample, said one or more parameters comprising shape of lines, linewidth, pitch, height and/or side wall angle of the periodic diffracting structure, said scatterometer comprising:

a reference database that includes a plurality of ellipsometric functions, each ellipsometric function corresponding to a set of values of said one or more parameters, said values including at least values of line width, height and side wall angle of periodic diffracting structures;

a source which emits broadband radiation;

a polarizer that polarizes the broadband radiation to produce a sampling beam sampling the periodic diffracting structure;

means for detecting ellipsometric parameters of a diffraction from the periodic diffracting structure of said broadband radiation over a range of wavelengths;

means for comparing said detected ellipsometric parameters to said plurality of ellipsometric functions in the database to determine said shape of lines, linewidth, pitch, height and/or side wall angle of the periodic diffracting structure, wherein said comparing means determines at least the line width, height and side wall angle of the periodic diffracting structure; and a device measuring data related to at least an index of refraction of a structure adjacent to and associated with the periodic diffracting structure.

21. The scatterometer of claim 20, said periodic diffracting structure located on a surface of a sample, wherein said associated structure is away from said periodic diffracting structure so that said data related to at least the index of refraction of the associated structure is measured without measuring said periodic diffracting structure and the comparing means uses said data related to at least the index of refraction of the associated structure to reduce number of parameters of the database and processing time for determining said parameters of the periodic diffracting structure.

22. The scatterometer of claim 20, wherein said device comprises a spectroscopic ellipsometer, spectrophotometer or spectroreflectometer.

23. The scatterometer of claim 20, wherein said device also measures thickness information of the associated structure.

24. The scatterometer of claim 20, wherein thickness of the associated structure is not a parameter in the reference database.

25. The scatterometer of claim 20, wherein the index of refraction of the associated structure is not a parameter in the reference database.

26. A scatterometer for measuring one or more parameters of a periodic diffracting structure of a sample, said one or more parameters comprising shape of lines, linewidth, pitch, height and/or side wall angle of the structure, said scatterometer comprising:
  a reference database that includes a plurality of signature curves, each signature curve corresponding to a set of values of said one or more parameters, said values including at least values of line width, height and side wall angle of periodic diffracting structures;
  a source which emits broadband radiation;
  a polarizer that polarizes the broadband radiation to produce a sampling beam at an oblique angle to the sample sampling the periodic diffracting structure;
  a detector detecting intensity data of a diffraction from the periodic diffracting structure of said broadband radiation over a range of wavelengths; and
  a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure, said periodic diffracting structure being on a surface of the sample, said reference database constructed using information related to at least an index of refraction or a film thickness of an associated structure away from said diffracting structure so that said film thickness of the associated structure is measurable without measuring said periodic diffracting structure.

27. A scatterometer for measuring one or more parameters of a periodic diffracting structure of a sample, said one or more parameters comprising shape of lines, linewidth, pitch, height and/or side wall angle of the structure, said scatterometer comprising:
  a reference database that includes a plurality of signature curves, each signature curve corresponding to a set of values of said one or more parameters, said values including at least values of line width, height and side wall angle of periodic diffracting structures;
  a source which emits broadband radiation;
  a polarizer that polarizes the broadband radiation to produce a sampling beam at an oblique angle to the sample sampling the periodic diffracting structure;
  a detector detecting intensity data of a diffraction from the periodic diffracting structure of said broadband radiation over a range of wavelengths; and
  a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure, said periodic diffracting structure being on a surface of the sample, said reference database constructed using optical properties of an associated structure away from said diffracting structure so that said optical properties of the associated structure are measurable without measuring said periodic diffracting structure to reduce the number of signatures curves in the reference database.

28. A scatterometer for measuring one or more parameters of a periodic diffracting structure of a sample, said one or more parameters comprising shape of lines, linewidth, pitch, height and/or side wall angle of the structure, said scatterometer comprising:
  a reference database that includes a plurality of signature curves, each signature curve corresponding to a set of values of said one or more parameters, said values including at least values of line width, height and side wall angle of periodic diffracting structures;
  a source which emits broadband radiation;
  a polarizer that polarizes the broadband radiation to produce a sampling beam at an oblique angle to the sample sampling the periodic diffracting structure;
  a detector detecting intensity data of a diffraction from the periodic diffracting structure of said broadband radiation over a range of wavelengths; and
  a processor comparing said detected intensity data to said plurality of signature curves in the reference database to determine said shape of lines, linewidth, pitch, height and/or side wall angle of the periodic diffracting structure, wherein said processor determines at least the line width, height and side wall angle of the periodic diffracting structure, said periodic diffracting structure being on a surface of the sample and away from said periodic diffracting structure, said scatterometer further comprising a device measuring data related to at least an index of refraction of the associated structure without measuring said periodic diffracting structure, wherein the processor uses said data related to at least the index of refraction of the associated structure to reduce number of parameters of the database and processing time for determining said one or more parameters of the periodic diffracting structure.

* * * * *